(12) United States Patent
Davis et al.

(10) Patent No.: US 11,672,546 B2
(45) Date of Patent: Jun. 13, 2023

(54) SURGICAL INSTRUMENT AND METHOD

(71) Applicant: WARSAW ORTHOPEDIC INC., Warsaw, IN (US)

(72) Inventors: Darren L. Davis, Arlington, TN (US); Eric C. Lange, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 267 days.

(21) Appl. No.: 17/220,162

(22) Filed: Apr. 1, 2021

(65) Prior Publication Data

US 2021/0212702 A1    Jul. 15, 2021

Related U.S. Application Data

(63) Continuation of application No. 16/409,600, filed on May 10, 2019, now Pat. No. 10,966,734.

(51) Int. Cl.
*A61B 17/16* (2006.01)
*A61B 17/00* (2006.01)

(52) U.S. Cl.
CPC ...... *A61B 17/1671* (2013.01); *A61B 17/1615* (2013.01); *A61B 17/1659* (2013.01); *A61B 2017/00398* (2013.01); *A61B 2017/00402* (2013.01); *A61B 2217/005* (2013.01); *A61B 2217/007* (2013.01)

(58) Field of Classification Search
CPC .................................................. A61B 17/1671
See application file for complete search history.

(56) References Cited

U.S. PATENT DOCUMENTS

| | | | |
|---|---|---|---|
| 5,383,884 A | 1/1995 | Summers | |
| 7,803,159 B2 | 9/2010 | Perez-Cruet et al. | |
| 9,867,646 B2* | 1/2018 | Baroud | A61M 5/142 |
| 2004/0191897 A1* | 9/2004 | Muschler | A61B 17/32002 |
| | | | 435/325 |
| 2008/0125783 A1* | 5/2008 | Perez-Cruet | A61B 17/32002 |
| | | | 606/82 |

(Continued)

FOREIGN PATENT DOCUMENTS

| | | |
|---|---|---|
| WO | 2013016698 A1 | 1/2013 |
| WO | 2014041540 A1 | 3/2014 |

OTHER PUBLICATIONS

European Search Report, App. No. 20806103.6, dated Nov. 21, 2023.

(Continued)

*Primary Examiner* — Christian A Sevilla
(74) *Attorney, Agent, or Firm* — Sorell, Lenna & Schmidt, LLP

(57) ABSTRACT

A surgical instrument includes a first member defining an axis and having a scraping surface configured to scrape tissue. A second member includes a cutting surface that is rotatable relative to the first member. The second member has a maximum length defined by opposite end surfaces of the second member. The end surfaces are each disposed within the first member. A third member includes an outer surface defining at least a portion of a passageway configured for disposal of the scraped tissue. The third member is fixed with the first member. The cutting surface is rotatable relative to the third member to transfer the scraped tissue along the axis. Systems and methods are disclosed.

20 Claims, 17 Drawing Sheets

(56) References Cited

U.S. PATENT DOCUMENTS

| | | | |
|---|---|---|---|
| 2008/0132929 A1* | 6/2008 | O'Sullivan | A61B 17/1615 606/170 |
| 2012/0136358 A1* | 5/2012 | Alleyne | A61B 17/1671 606/83 |
| 2016/0066946 A1* | 3/2016 | To | A61B 17/3205 606/171 |
| 2016/0331645 A1 | 11/2016 | Bagwell et al. | |
| 2017/0196588 A1 | 7/2017 | Schuman et al. | |
| 2018/0049764 A1 | 2/2018 | Yoon et al. | |
| 2018/0317939 A1* | 11/2018 | Davis | A61B 17/1671 |

OTHER PUBLICATIONS

Patent Cooperation Treaty, International Search Report, Written Opinion of the International Searching Authority Intl. Appl. No. PCT/US2020/030582, dated Oct. 22, 2020.

* cited by examiner

SURGICAL INSTRUMENT AND METHOD

CROSS REFERENCE TO RELATED APPLICATIONS

This application is a continuation of U.S. patent application Ser. No. 16/409,600, filed May 10, 2019, which is expressly incorporated by reference herein, in its entirety.

TECHNICAL FIELD

The present disclosure generally relates to medical devices for the treatment of musculoskeletal disorders, and more particularly to a surgical system for preparation of a surgical site and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior art technologies.

SUMMARY

In one embodiment, a surgical instrument is provided. The surgical instrument includes a first member defining an axis and having a scraping surface configured to scrape tissue. A second member includes a cutting surface that is rotatable relative to the first member. The second member has a maximum length defined by opposite end surfaces of the second member, the end surfaces each being disposed within the first member. A third member includes an outer surface defining at least a portion of a passageway configured for disposal of the scraped tissue. The third member is fixed with the first member. The cutting surface is rotatable relative to the third member to transfer the scraped tissue along the axis. Systems and methods of use are disclosed.

In one embodiment, a surgical instrument is provided. The surgical instrument includes a housing defining a longitudinal axis and having an inner surface that defines a cavity. The housing further includes a plurality of teeth disposed along a wall that extends transverse to the longitudinal axis, the teeth being configured to scrape tissue. An auger comprises a rotatable cutter having a maximum length defined by opposite end surfaces, the end surfaces each being disposed within the cavity. The rotatable cutter is rotatable relative to the housing. The rotatable cutter defines an interior cavity. The auger further comprises a stationary member disposed within the interior cavity and fixed with the housing. The stationary member includes a helical outer surface such that the rotatable cutter rotates about the helical outer surface to transfer the scraped tissue in a first direction along the axis.

In one embodiment, a surgical instrument is provided. The surgical instrument includes a first member defining an axis and having spaced apart cutting surfaces each extending transverse to the axis. The cutting surfaces are configured to scrape tissue and define an opening therebetween. A second member is fixed relative to the first member. A third member includes a cutting surface that is rotatable relative to the second member and an inner surface defining at least a portion of a passageway configured for disposal of the scraped tissue. The third member has a maximum length defined by opposite end surfaces, the end surfaces each being disposed within the first member. The cutting surface is rotatable to transfer the scraped tissue along the axis.

BRIEF DESCRIPTION OF THE DRAWINGS

The present disclosure will become more readily apparent from the specific description accompanied by the following drawings, in which.

DETAILED DESCRIPTION

Figure 1:
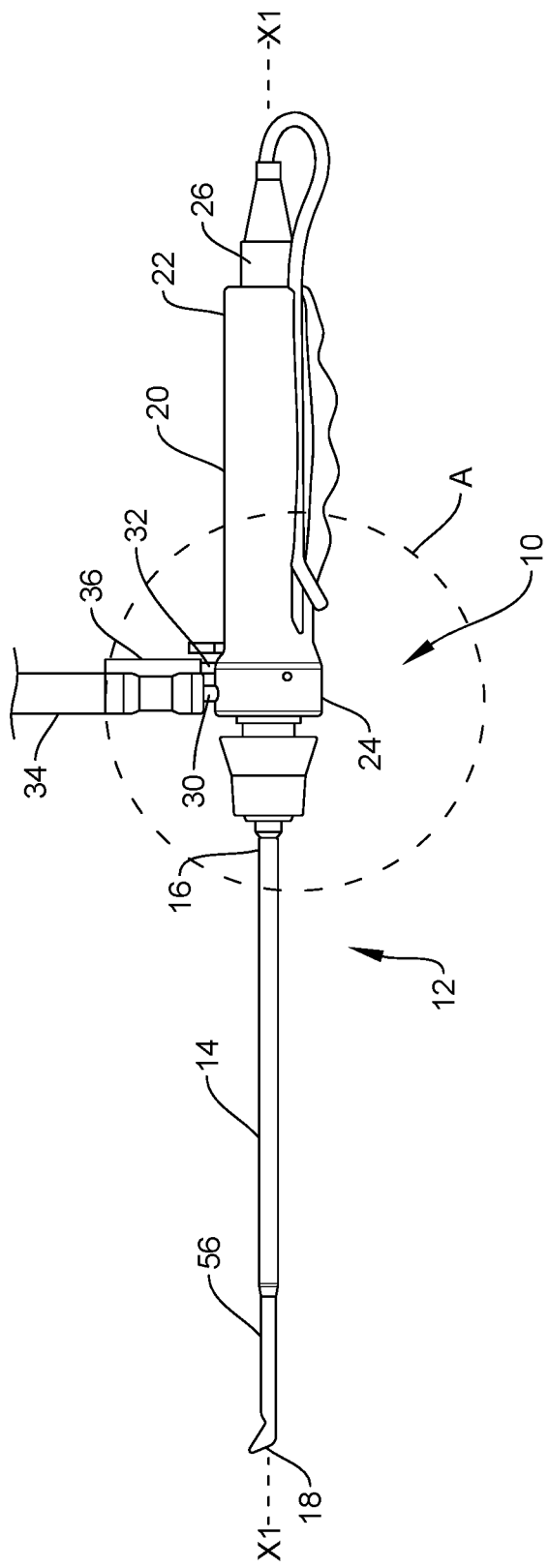
FIG. 1 is a side view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a surgical system for preparation of a surgical site and a method for treating a spine.

In one embodiment, the surgical system includes a surgical instrument, such as, for example, a disc preparation instrument. In some embodiments, the surgical instrument includes a scraper tube disposed about a rotating helical blade. A stationary auger is positioned within the rotating helical blade. The rotating helical blade defines an irrigation pathway therein. Tissue that is scraped by the scraper tube is pulled into the rotating helical blade. The stationary auger transfers the scraped tissue under the rotating helical blade, which cuts the scraped tissue into a smaller size. A suction pathway between the irrigation tube and the scraper tube transfers the cut tissue to a remote container. In some embodiments, the system includes various aspects, which influence the capturing of tissue. For example, in a first aspect, tissue is captured mechanically between the helical blades relative to the scraper tube. In a second aspect, the rotation of the helical blade with respect to the inner auger and outer tube causes a pumping action, which creates a different pressure across the blade and induces a negative pressure (vacuum) at the opening of the tube, which can draw tissue into the cutter. In a third aspect, there is a direct passageway from the opening of the tube through the channels of the cutter/auger to the suction container, which will draw tissue effluent through the system.

In one embodiment, the surgical instrument is configured for efficient grinding and removal of the tissue via the cutting mechanism described herein. A grinder end of the rotating shaft allows better tissue removal. Further, when the tissue enters into the auger it has only been through one cut. A ring band in the surgical instrument cuts the tissue a second time as it exits the rotating shaft, which makes it easier to liquefy with the irrigation. In one embodiment, the surgical instrument includes a channel/pocket on the side allows the device to be more aggressive and grab the tissue and pull it into the disposal.

In one embodiment, the surgical system includes a surgical instrument that includes a manual cutter housing disposed about an internal rotating cutter. In some embodiments, the surgical system includes a disc preparation device with a combination of an outer paddle scraper structure having teeth and an internal rotating auger and/or suction mechanism for conveying disc debris into the instrument and away from the surgical site.

In some embodiments, the surgical system includes a surgical instrument including a scraper housing that provides a rigid protective cover configured to cover the rotating cutter blade. In some embodiments, the scraper housing includes teeth to facilitate scraping of peripheral material. In some embodiments, the surgical instrument includes a housing configured to incorporate one, two, and/or multiple walls or surfaces with teeth to facilitate scraping of the peripheral material. In some embodiments, the surgical instrument includes a rotating cutter mechanism disposed with the scraping cutter housing for cutting and/or macerating disc material. In some embodiments, the surgical instrument includes suction to facilitate material removal. In one embodiment, the surgical instrument includes a navigation device to facilitate positioning and/or tracking of components of the surgical system.

In some embodiments, the surgical instrument is configured to be surgically inserted into a space between vertebral bodies to facilitate scraping and removing tissue and bone to create a space or pathway for fusion or motion implants. In some embodiments, the surgical instrument includes a scraper housing, a rotating cutter, a stationary auger and an irrigation and/or debris removal tube.

In one embodiment, the surgical instrument includes a rotating cutter having a circumferential helical cutting geometry that is configured to create shear against an inside portion of the housing. In some embodiments, the helical shape can be either a right hand or left hand cutter feature. In some embodiments, the surgical instrument includes a cannulated rotatable cutter to facilitate mating with a stationary auger. In some embodiments, the surgical instrument includes a rotor/stator combination to facilitate high shear to process cut material into a smaller particle size. In some embodiments, the helical shape causes scraped debris to channel inside the stationary auger. In some embodiments, the surgical instrument includes a rotating cutter having an end configured with a cutting geometry. In some embodiments, the surgical instrument includes irrigation surfaces that facilitate irrigation to enter the auger channels to mix with debris to provide a transfer mixture, and create a hydraulic bearing surface between moving parts of the cutter.

In one embodiment, the surgical instrument includes a stationary auger member that includes a rotational pitch opposite of the cutter to create a force along auger channels to transfer cut material towards a rotating grinder. In some embodiments, the auger is cannulated to facilitate irrigation to transfer to a tip of the rotating cutter. In some embodiments, the surgical instrument includes a rotating cutter having irrigation and/or a hydraulic bearing surface and irrigation holes.

In one embodiment, the surgical instrument includes debris irrigation and suction. In one embodiment, the surgical instrument includes a manual scraper with a spinning cutter having an internal stationary auger. In some embodiments, the surgical instrument includes an irrigation port disposed in a handle and a suction connection in the handle. In one embodiment, the manual blade includes cutting/scraping elements. In one embodiment, the manual scraper includes teeth to facilitate scraping of tissue. In one embodiment, the surgical instrument includes scraper teeth or blades and rotating blades. In one embodiment, the surgical instrument is employed with a method such that a surgeon scrapes away disc and endplate tissue with the manual scraper. In some embodiments, the method includes the step of moving tissue debris into ports.

In some embodiments, components of the surgical instrument have a central cannula configured for disposal of an illumination device. In some embodiments, the illumination device includes a fiber-optic light cable. In some embodiments, components of the surgical instrument include a fiber-optic light and a camera mounted with an outer housing and/or a stationary shaft, as described herein. In some embodiments, the camera includes a miniature camera.

In some embodiments, the surgical instrument includes an auger comprising two or more counter rotating internal blades. In some embodiments, the blades are co-axially disposed and comprise alternate diameters, increasing or decreasing. In some embodiments, the blades are separate and disposed in a serial configuration. In some embodiments, the blades may rotate in the same or different directions.

In some embodiments, the surgical instrument includes a manual scraper housing that collects tissue debris, as described herein, and arrests movement of the components of the surgical system to close and seal the surgical instrument. In some embodiments, this configuration increases a suction force to facilitate removal of tissue debris from the scraper and/or blades. In some embodiments, the components of the surgical instrument can be heated and/or cooled to facilitate processing of tissue, as described herein. In some embodiments the surgical instrument includes an inner blade, such as, for example, the stationary shaft, having a heating or cooling element that heats or freezes tissue, such as, for example, intervertebral disc tissue and an outer blade, such as, for example, the rotatable cutter, having an insulating element disposed about the inner blade. The heating or cooling element can be electrically connected to a power source.

In some embodiments, the cutting surfaces or blades of the components of the surgical instrument, as described herein, can include, such as, for example, diamonds, teeth, spikes and/or sandpaper. In some embodiments, the surgical system includes a diverting filter connected to the surgical instrument and configured to bifurcate tissue debris into a plurality of portions of the filter. In some embodiments, the filter includes at least one portion that facilitates trapping and collecting bone.

In some embodiments, the surgical system includes a device configured to inject a bio-material, such as, for example, a polymer, cement, or stiffener into intervertebral disc tissue. In some embodiments, the bio-material is injected with tissue to quick set at the time of surgery or prepared and introduced before the surgery. In some embodiments, the surgical system includes a bio-material, such as, for example, a discogram injection to stiffen intervertebral disc tissue and increase cutting efficiency. In some embodiments, the surgical system is employed with a method such that intervertebral disc tissue is heated and/or bio-frozen prior to cutting to alter the disc material characteristics and to facilitate cutting.

In one embodiment, one or all of the components of the surgical system are disposable, peel-pack, pre-packed sterile devices that can be used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-25, there are illustrated components of a surgical system 10 including a surgical instrument 12.

The components of surgical system 10 can be fabricated from biologically acceptable materials suitable for medical applications, including metals, synthetic polymers, ceramics and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), calcium sulfate, or other resorbable polymers such as polyaetide, polyglycolide, polytyrosine carbonate, polycaroplaetohe and their combinations. In some embodiments, one or more components of surgical system 10 may be fabricated from piezoelectric materials.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 including surgical instrument 12 can be employed, for example, with mini-open and open surgical techniques to prepare a surgical site including tissue in connection with a surgical procedure for delivery and introduction of instrumentation and/or an implant, such as, for example, an intervertebral implant, at a surgical site within a body of a patient, for example, a section of a spine. In one embodiment, surgical system 10 may be employed with surgical procedures, such as, for example, corpectomy and discectomy, which include fusion and/or fixation treatments that employ implants.

Surgical instrument 12 includes a member, such as, for example, a scraper tube 14 that extends between an end 16 and an end 18. Tube 14 defines an axis X1. Surgical instrument 12 includes a handle 20 coupled to tube 14 such that handle 20 is fixed relative to tube 14. That is, tube 14 and handle 20 are coupled to one another such that translation and/or rotation of tube 14 relative to handle 20 is prevented. As such, rotation of handle 20 also rotates tube 14 and translation of handle 20 also translates tube 14. This allows handle 20 to be gripped by a medical practitioner and manipulated to scrape and/or distract tissue using end 18 of tube 14, as discussed herein. In some embodiments, handle 20 is removably coupled to tube 14 such that handle 20 may be removed from tube 14 without breaking handle 20 or tube 14. In some embodiments, handle 20 is permanently coupled to tube 14 such that handle 20 cannot be removed from tube 14 without breaking handle 20 and/or tube 14. In some embodiments, handle 20 is integrally and/or monolithically formed tube 14. In some embodiments, tube 14 and/or handle 20 may have cross section configurations, such as, for example, oval, cylindrical, triangular, square, polygonal, irregular, uniform, non-uniform, offset, staggered, undulating, arcuate, variable and/or tapered. In some embodiments, tube 14 is a bayonet style tube that is configured to position handle 20 out of the line of site of tube 14.

Handle 20 includes an end 22 and an opposite end 24. A motor 26 is coupled to end 22. Motor 26 is configured to rotate a member, such as, for example, an auger or blade assembly 28 relative to tube 14 about axis X1, as discussed herein. End 24 includes a port 30 and a port 32 that is spaced apart from port 30. A suction tube 34 is coupled to port 30. Tube 34 is configured to create suction within a suction pathway of tube 14 to transfer scraped tissue within the suction pathway to a remote container, as discussed herein.

Figure 1A:
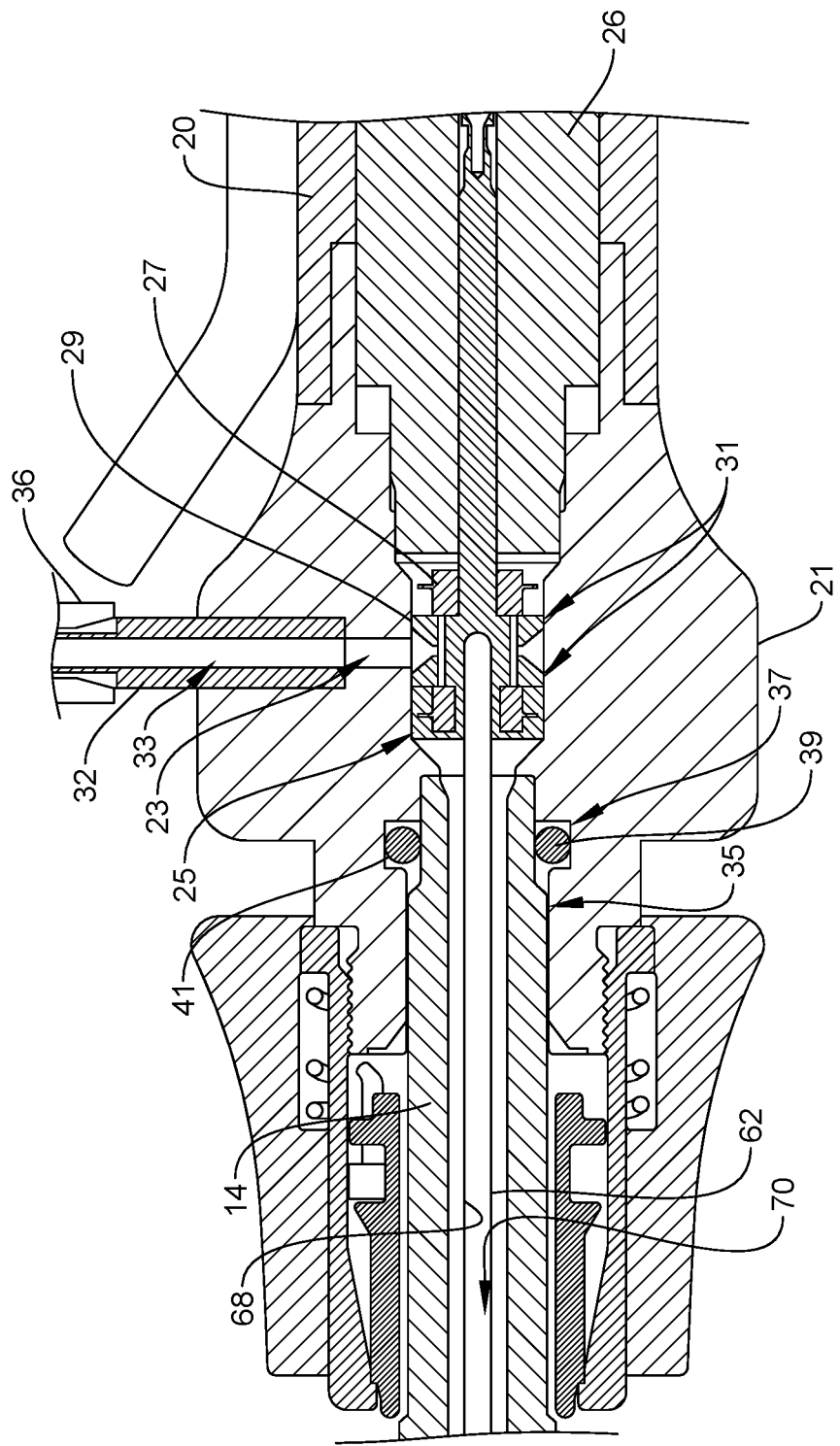
FIG. 1A is a side, cross sectional view of components of the surgical system shown in FIG. 1 of detail A in FIG. 1.
Figure 2:
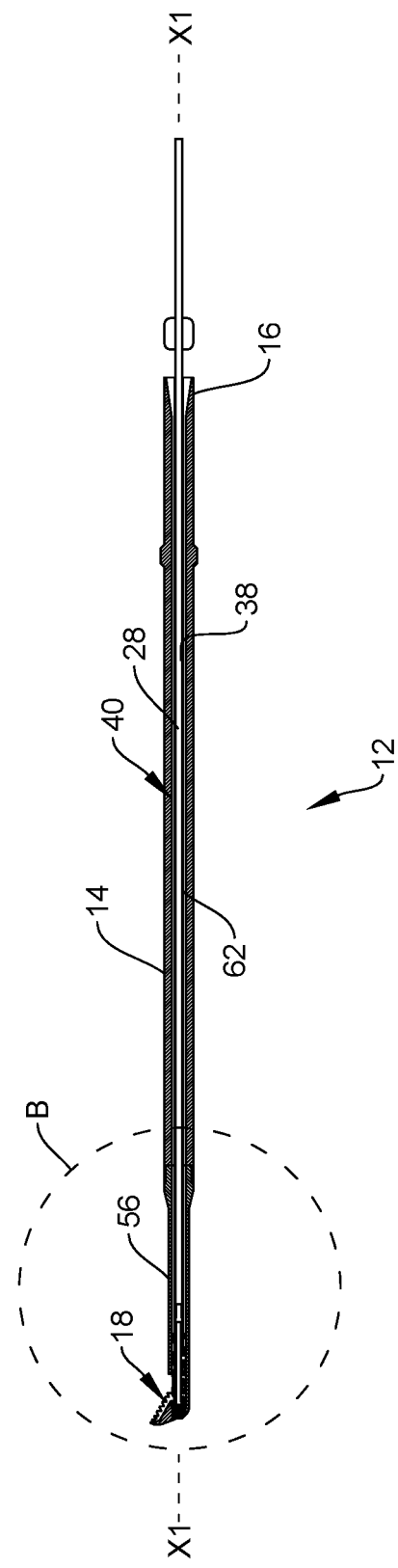
FIG. 2 is a side, cross sectional view of components of the system shown in FIG. 1.

In some embodiments, tube 34 is in communication with a channel 40 of tube 14. A suction cannister/pump system is connected with tube 34 such that the suction cannister/pump system provides suction within channel 40 to move material within channel 40 in the direction D1 in FIG. 3 out of channel 40 and the into suction cannister/pump system. An irrigation tube 36 is coupled to port 32. Tube 36 is configured to provide a stream of water or other fluid within an irrigation pathway of blade assembly 28 that mixes with debris to provide a transfer mixture that is removed from instrument 12 via suction tube 34, as discussed herein. In some embodiments, handle 20 includes a hub 21. Port 32 and tube 36 extend through hub 21, a shown in FIG. 1A, for example. Hub 21 includes a conduit 23 that is in communication with a channel 33 of port 32 and a cavity 25 that is in communication with conduit 23 and channel 33. An adapter 27 and an end of tube 14 are positioned within cavity 25 such that a lumen 29 of adapter 27 is in communication with a passageway 70 and conduit 23 such that a fluid or other material can be introduced through channel 33, conduit 23 and lumen 29 and into passageway 70 to direct the fluid to blade assembly 28, as discussed herein. In some embodiments, system 10 includes one or a plurality of irrigation seals 31 to direct the fluid into passageway 70, as shown in FIG. 1A, for example.

Tube 14 includes an inner surface 38 that defines a cavity, such as, for example, channel 40. Channel 40 is configured for disposal of a member, such as, for example, blade assembly 28, as described herein. In some embodiments, channel 40 may have various cross section configurations, such as, for example, circular, cylindrical, oval, oblong, triangular, rectangular, square, polygonal, irregular, uniform, non-uniform, variable, tubular and/or tapered. In some embodiments, tube 14 and/or handle 20 is/are configured to provide a rigid protective cover for blade assembly 28. In some embodiments, tube 14 is removably coupled to handle 20 such that tube 14 can be removed from handle 20 without breaking handle 20 and/or tube 14. In some embodiments, hub 21 includes an aperture 35 configured for disposal of tube 14 and a recess 37 that is in communication with aperture 35, as shown in FIG. 1A, for example. A band, such as, for example, a ring 39 is positioned within recess 37 and a groove 41 of tube 41 to connect tube 14 with hub 21. In some embodiments, tube 14 is integrally and/or monolithically formed with handle 20 such that tube 14 cannot be removed from handle without breaking handle 20 and/or tube 14.

Figure 4:
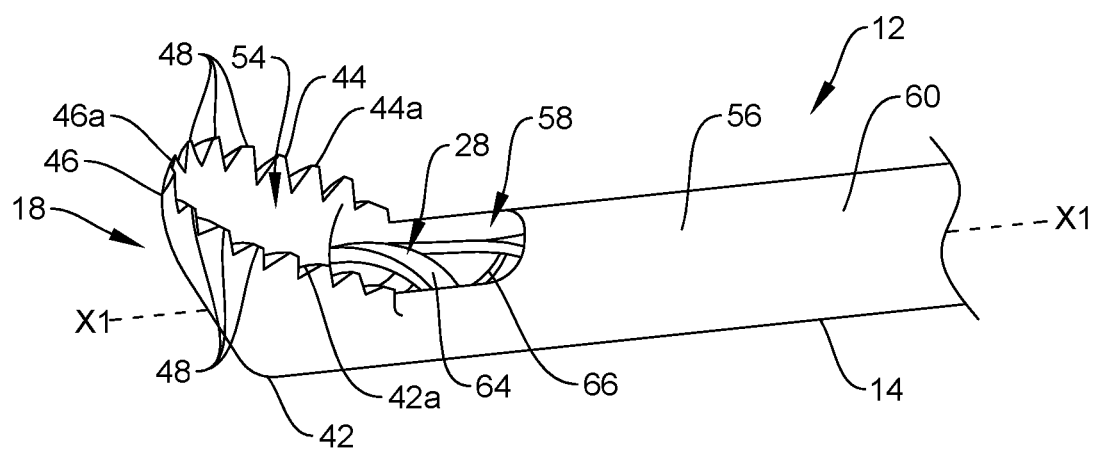
FIG. 4 is a perspective view of components of the system shown in FIG. 1.
Figure 5:
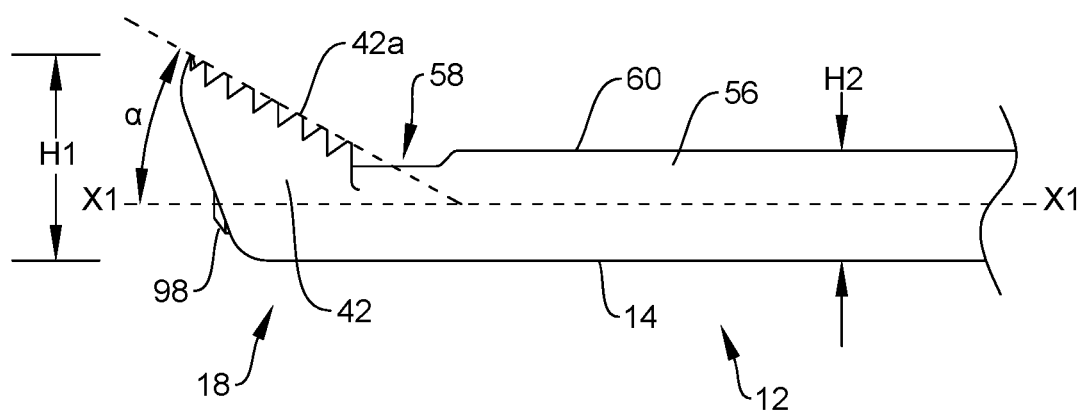
FIG. 5 is a side view of components of the system shown in FIG. 1.
Figure 6:
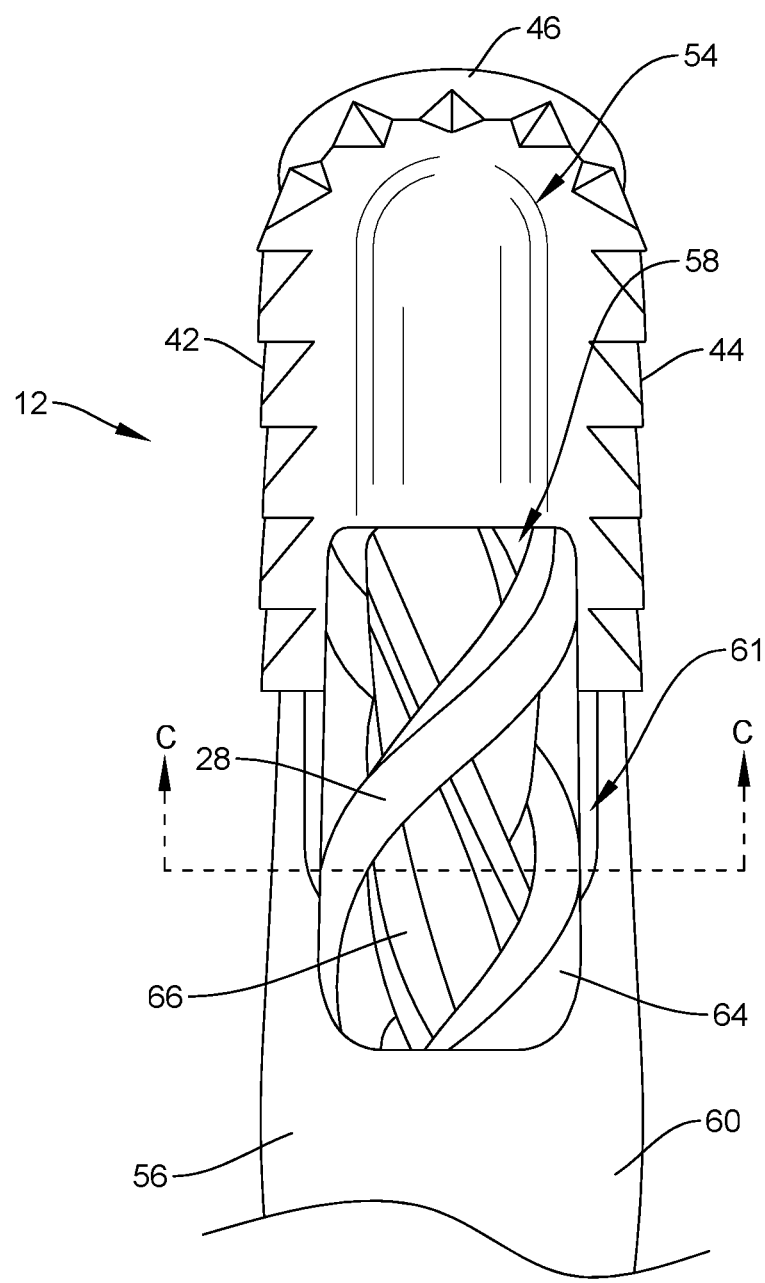
FIG. 6 is a top view of components of the system shown in FIG. 1.
Figure 7:
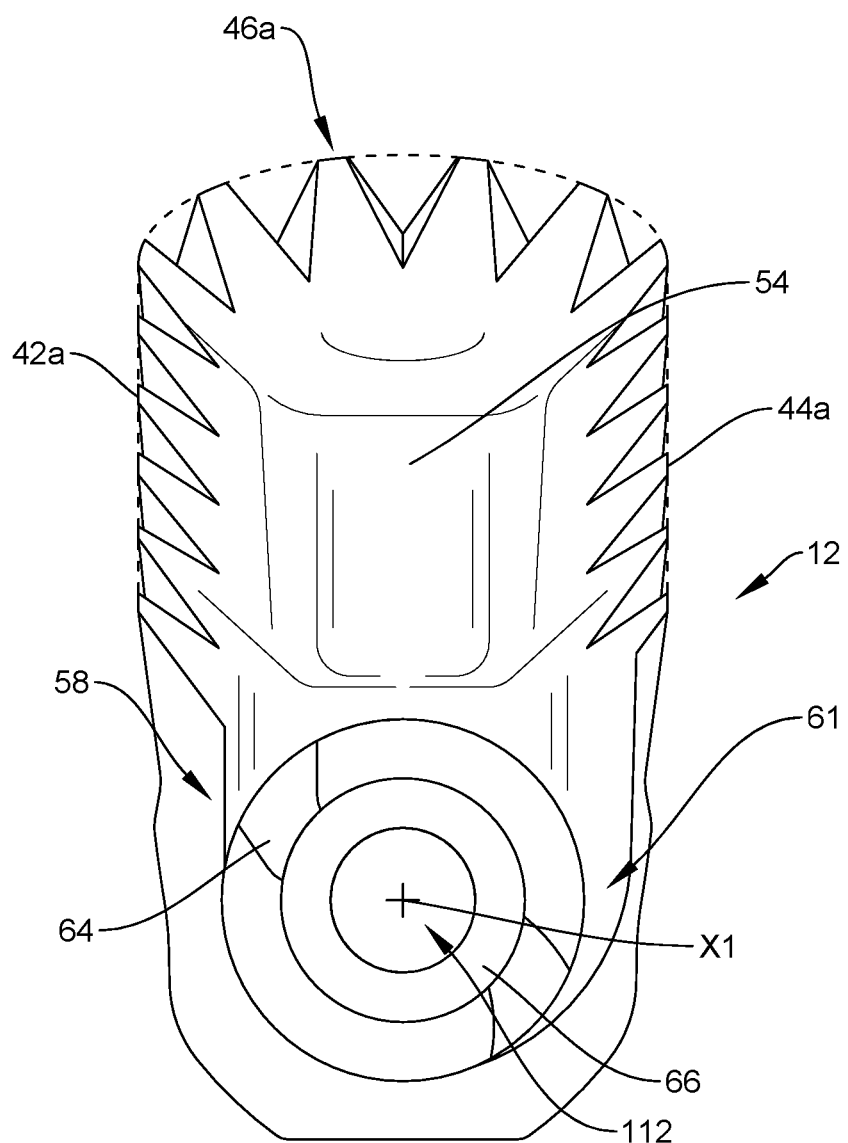
FIG. 7 is a cross sectional view taken along lines C-C shown in FIG. 6.
Figure 8:
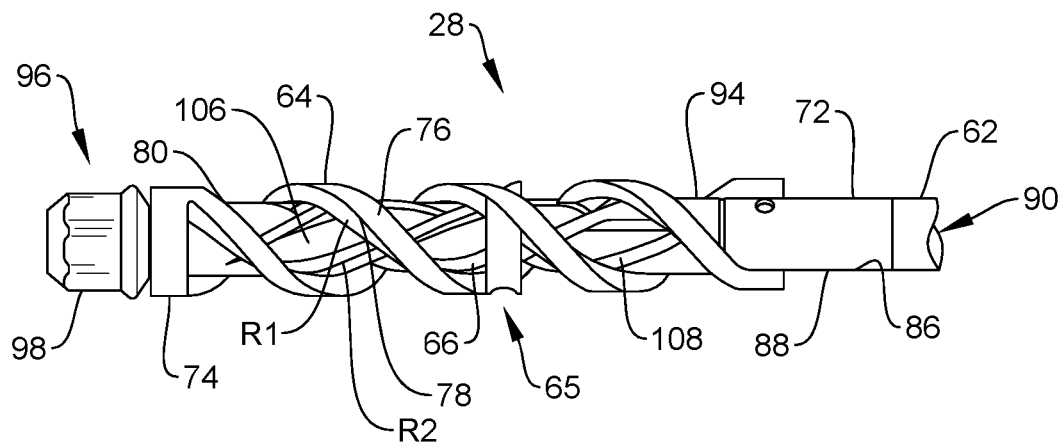
FIG. 8 is a side view, in part phantom, of components of the system shown in FIG. 1.

End 18 of tube 14 includes spaced apart side walls 42, 44 that are connected by a transverse wall 46, as best shown in FIGS. 4, 6 and 7. That is, wall 46 extends from wall 42 to wall 44 to join wall 42 with wall 44. In some embodiments, wall 46 is continuously curved. That is, wall 46 is continuously curved from wall 42 to wall 44 and/or has a continuous radius of curvature from wall 42 to wall 44. At least a portion of each of walls 42, 44, 46 extends transverse to axis X1. That is, upper edges 42a, 44a, 46a of walls 42, 44, 46 each extends transverse to axis X1. In some embodiments, edges 42a, 44a, 46a define a cutting surface, such as, for example, a scraping surface configured to scrape tissue, such as, for example, bone, as discussed herein. Edge 42a extends parallel to edge 44a along the entire lengths of edges 42a, 44a. Edge 46a extends transverse to edges 42a, 44a. In some embodiments, edges 42a, 44a are each disposed at an angle α relative to axis X1, as shown in FIG. 5 to facilitate scraping and/or disrupting material, such as, for example, tissue and to dispose the material within tube 14, as discussed herein. In some embodiments, angle α is an acute angle. In some embodiments, angle α may include an angle in a range of 0 through 90 degrees. In some embodiments, angle α may include an angle in a range of 0 through 120 degrees. In some embodiments, angle α may include an angle in a range of 0 through 150 degrees. In some embodiments, angle α may include an angle in a range of 0 through 180 degrees. In some embodiments, edge 46a is continuously curved. That is, edge 46a is continuously curved from edge 42a to edge 44a and/or has a continuous radius of curvature from edge 42a to edge 44a.

A plurality of teeth 48 are disposed along walls 42, 44, 46. Teeth 48 are configured to disrupt, scrape and/or remove tissue from a surgical site, as discussed herein. In some embodiments, tips 50 of teeth 48 define edges 42a, 44a, 46a. In some embodiments, tips 50 are planar such that teeth 48 resemble truncated triangles. In some embodiments, tips 50 are pointed such that teeth 48 resemble isosceles triangles or equilateral triangles. Adjacent teeth 48 define gaps 52 therebetween. As such, edges 42a, 44a, 46a are interrupted by gaps 52 along the lengths of edges 42a, 44a, 46a. In some embodiments, teeth 48 are arranged uniformly along walls 42, 44, 46, such that gaps 52 are uniformly spaced apart from one another along walls 42, 44, 46. Inner surfaces of walls 42, 44, 46 define a cavity 54 configured for disposal of material, such as, for example, tissue that is scraped by teeth 48, as discussed herein. Manipulation including translation and/or angulation of tube 14 causes teeth 48 to disrupt, scrape, cut and/or remove tissue at a surgical site and guide tissue into cavity 54. In some embodiments, teeth 48 are configured for disposal between vertebral bodies to disrupt, scrape, cut and/or remove tissue, such as, for example, intervertebral disc tissue and/or vertebral endplate tissue to create a cavity, space and/or pathway at a surgical site including a targeted portion of an anatomy for delivery, introduction and/or implantation of a spinal implant. In some embodiments, wall 46 includes an inner surface 46a that extends transverse to axis X1. Surface 46a is angled to direct material in cavity 54 into an opening of tube 14, as discussed herein. In some embodiments, walls 42, 44, 46 are free of teeth, such as, for example, teeth 48. That is, adjoining surfaces of walls 42, 44, 46 are planar and continuous. In some embodiments, the disruption, scraping, cutting and/or removal of tissue provided by teeth 48 may, in combination with teeth 48 or alternatively, be provided by piezoelectric features or materials.

Walls 42, 44, 46 each extend from a shaft 56 of tube 14. Shaft 56 extends parallel to axis X1 along the entire length of shaft 56. End 18 has a maximum height H1 that is greater than a maximum height H2 of shaft 56, as shown in FIG. 5. Shaft 56 includes an opening 58 that extends through a wall thickness of shaft 56, the wall thickness of shaft 56 being defined by surface 38 and an opposite outer surface 60 of shaft 56. Opening 58 is in communication with channel 40 and configured for disposal of material, such as, for example, tissue in cavity 54 that was scraped and/or cut by teeth 48 to move the material through opening 58 and into channel 40. As discussed herein, surface 46a is angled to move material from cavity 54 through opening 58 and into channel 40.

In some embodiments, opening 58 includes an inlet 61 positioned on one side of blade assembly 28, as best shown in FIGS. 6 and 7. Inlet 61 is configured to allow blade assembly 28 to rotate within channel 40. That is, when blade assembly 28 comprises a right-handed helical blade and is rotated in a first rotational direction, such as, for example, clockwise, at least a portion of the right-handed helical blade will occupy and rotate within inlet 61. In some embodiments, blade assembly 28 comprises a left-handed helical blade and inlet 61 is positioned on an opposite side of blade assembly 28 such that rotation of the left-handed helical blade causes at least a portion of the left-handed helical blade to occupy and rotate within inlet 61. Opening 58 includes only one inlet 61 positioned on one side of blade assembly 28 such that opening is asymmetrical. As stated above, the side of blade assembly 28 that inlet 61 is positioned on is dependent on whether blade assembly 28 comprises a right-handed helical blade or a left-handed helical blade. Significantly, including one inlet 61 positioned on one side of blade assembly 28 allows scraped and/or cut tissue to be suctioned toward a distal end of channel 40, such as, for example, toward a rotating grinder that grinds the scraped and/or cut tissue. Indeed, it has been found that if opening 58 includes an inlet on both sides of blade assembly 28, scraped and/or cut tissue is prevented from being suctioned toward the distal end of channel 40. That is, if opening 58 includes an inlet on both sides of blade assembly 28, scraped and/or cut tissue will become clogged within channel 40, thus preventing the scraped and/or cut tissue from being ground by a grinder within channel 40.

Blade assembly 28 is configured for disposal in channel 40 such that blade assembly 28 is visible through opening 58. Blade assembly 28 includes a shaft 62 that is configured to be coupled to motor 26 to rotate shaft 62 relative to tube 14 about axis X1. In some embodiments, shaft 62 is removably coupled to motor 26 such that shaft 62 can be removed from motor 26 without breaking shaft 62 and/or motor 26. In some embodiments, shaft 62 is permanently fixed with motor 26 such that shaft 62 cannot be removed from motor 26 without breaking shaft 62 and/or motor 26. For example, in some embodiments, shaft 62 is integrally and/or monolithically formed with an output shaft of motor 26. Shaft 62 extends along axis X1 when disposed in channel 40. Blade assembly 28 includes a member, such as, for example, a rotatable cutter 64 that is coupled to shaft 62 and a member, such as, for example, a stationary auger 66. In some embodiments, auger 66 is integrally and/or monolithically formed with tube 14 such that auger 66 is permanently affixed to tube 14.

Figure 3:
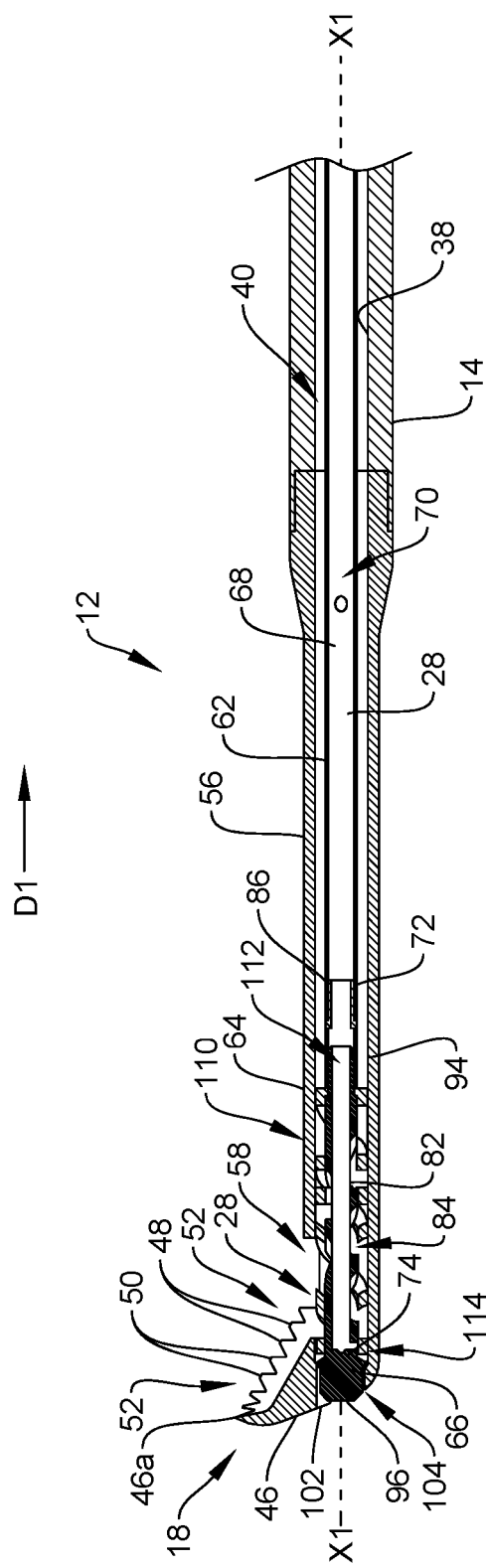
FIG. 3 is a side, cross sectional view of components of the surgical system shown in FIG. 1 of detail B in FIG. 2.

Cutter 64 is fixed relative to shaft 62 such that rotation of shaft 62 relative to tube 14 about axis X1 also rotates cutter 64 relative to tube 14 about axis X1. In some embodiments, shaft 62 is removably coupled to cutter 64 such that shaft 62 can be removed from cutter 64 without breaking shaft 62 and/or cutter 64. In some embodiments, shaft 62 is permanently fixed with cutter 64 such that shaft 62 cannot be removed from cutter 64 without breaking shaft 62 and/or cutter 64. For example, in some embodiments, shaft 62 is integrally and/or monolithically formed with cutter 64. Shaft 62 includes an inner surface 68 defining a passageway 70, as best shown in FIG. 3. In some embodiments, an end 72 of cutter 64 is positioned within passageway 70 such that an outer surface of end 72 directly engages surface 68 to fix cutter 64 relative to shaft 62. In embodiments, cutter 64 can be variously connected with shaft 62, such as, for example, monolithic, integral connection, frictional engagement, threaded engagement, mutual grooves, screws, adhesive, nails, barbs and/or raised element. Cutter 64 extends between end 72 and an opposite end 74. Cutter 64 extends along axis X1 when disposed in channel 40. Cutter 64 is tubular in configuration. In some embodiments, cutter 64 may have cross section configurations, such as, for example, oval, cylindrical, triangular, square, polygonal, irregular, uniform, non-uniform, offset, staggered, undulating, arcuate, variable and/or tapered.

Cutter 64 includes a surface 76 that defines a plurality of spaced cutting flutes 78. Cutting flutes 78 are spaced along cutter 64 and form helical blades 80 extending along a length of cutter 64. Helical blades 80 are disposed at a rotational pitch R1. In some embodiments, surface 76 includes a scaffold and/or network of blades. In some embodiments, blades 80 may be disposed at alternate relative orientations, such as, for example, parallel, transverse and/or other angular orientations such as acute or obtuse, co-axial and/or may be offset or staggered. Blades 80 are configured for rotation within channel 40 and about auger 66 to disrupt, scrape, cut, shear and/or macerate tissue and/or transfer and/or convey tissue along auger 66, as described herein. In some embodiments, cutter 64 includes a section, such as, for example, a solid ring section 65, shown in FIG. 8, for example. Section 65 is configured to force tissue under cutter 64 and through flutes of auger 66 defined by a helical surface 108 of auger 66. This controls the tissue entering a discharge side of cutter 64 into a suction and/or vacuum pathway, as discussed herein.

Cutter 64 includes an inner surface 82 that defines an interior cavity 84. Cavity 84 is in communication with passageway 70. In some embodiments, cavity 84 is coaxial with passageway 70. Cavity 84 is configured for disposal of auger 66 within channel 40, as described herein. Cutter 64 is configured for rotation relative to tube 14 and auger 66 to transfer tissue along a first direction, such as, for example, a direction D1 (FIG. 9) along axis X1, as described herein. In some embodiments, blades 80 rotate relative to tube 14 and auger 66 within channel 40 to move tissue in cavity 54 that was disrupted, scraped, cut, sheared and/or macerated by teeth 48 into a smaller particle size for removal from a surgical site. In some embodiments, blades 80 rotate such that tissue disposed adjacent and/or between cutter 64 and auger 66 is transferred and/or conveyed in direction D1 due to fluid transfer forces created between the helical configurations of cutter 64 and auger 66. The tissue is transferred and/or conveyed for removal from a surgical site, as described herein. In some embodiments, auger 66 comprises two or more counter rotating internal blades, similar to cutter 64. In some embodiments, the blades are co-axially disposed and comprise alternate diameters, increasing or decreasing. In some embodiments, the blades are separate and disposed in a serial configuration. In some embodiments, the blades may rotate in the same or different directions. End 72 includes a surface 86 and a surface 88. Surface 86 defines an opening 90 that is communication with passageway 70. Blade assembly 28 is configured to have fluid flow through passageway 70 and opening 90 and into auger 66, as described herein.

Auger 66 extends between an end 94 and an end 96 along axis X1 when disposed in channel 40. Auger 66 is configured for disposal with cavity 84. Auger 66 is fixed with end 18 of tube 14. That is, auger 66 is coupled to tube 14 such that auger 66 is prevented from rotating and/or translating relative to tube 14. In some embodiments, end 96 includes an engagement portion 98 configured for engagement with tube 14 to fix auger 66 relative to tube 14. In some embodiments, portion 98 may include a square, triangular, polygonal, star, torx, or hexalobe cross sectional configuration configured engage a correspondingly shaped portion of tube 14, such as, for example, a surface 102 of tube. For example, in some embodiments, surface 102 defines an aperture 104 having a cross section that corresponds to the cross sectional configuration of portion 98 to resist and/or prevent rotation of auger 66 relative to tube 14. In some embodiments, portion 98 is positioned within aperture 104 such that an outer surface of portion 98 directly engages surface 102 to resist and/or prevent rotation of auger 66 relative to tube 14. In some embodiments, portion 98 extends through aperture 104 such that a section of portion 98 is positioned outside of tube 14, as shown in FIG. 3, for example.

Auger 66 includes a surface 106 that defines helical surface 108. Helical surface 108 is disposed in an alternate orientation relative to helical blades 80. Helical surface 108 includes a rotational pitch R2 that is alternative to rotational pitch R1 to create a dynamic fluid transfer and/or shear force or pressure to transfer and/or convey tissue from a surgical in direction D1. Helical blades 80 and helical surface 108 form a transfer channel 110 therebetween configured to direct cut tissue along axis X1 in direction D1. The dynamic fluid transfer and/or shear force created by rotation of cutter 64 relative to auger 66 and between helical blades 80 and helical surface 108 direct fluid flow and scraped or cut tissue within transfer channel 110. In some embodiments, surface 76 and/or surface 106 may comprise alternate configurations, such as, for example, grooved, channeled, undulating, even, uniform, non-uniform, offset, staggered, textured and/or tapered to facilitate directional flow of fluid. In one embodiment, auger 66 includes fiber-optic light cable (not shown) disposed and/or helically wound through a surface of auger 66. The light-cable illuminates a surgical site. In some embodiments, an illumination device may be mounted with various components of surgical instrument 12. In one embodiment, a miniature camera (not shown) can be mounted with various components of surgical instrument 12 to facilitate imaging of the surgical site.

Figure 9:
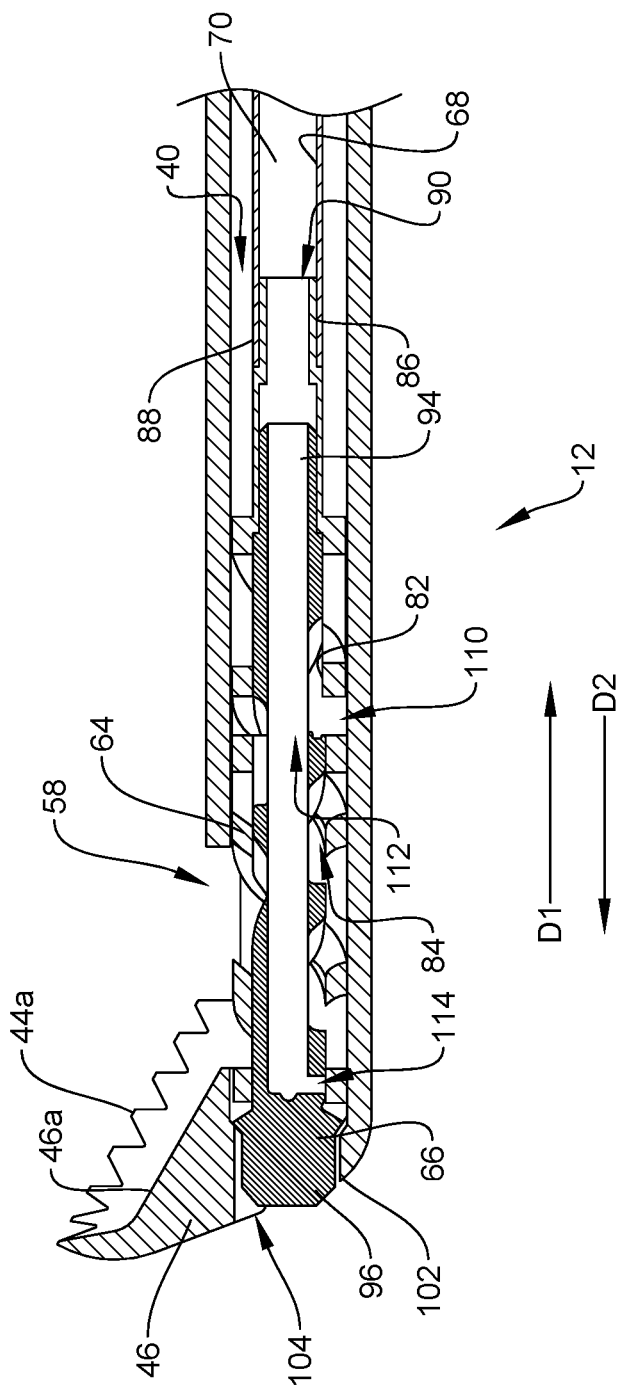
FIG. 9 is a side, cross sectional view of components of the system shown in FIG. 1.

In some embodiments, auger 66 is cannulated and defines a passageway 112 configured for transfer of fluid in a direction, such as, for example, a direction D2 shown in FIG. 9. Passageway 112 is in communication with passageway 70 via opening 90, as described herein. Auger 66 defines at least one opening 114 configured to direct fluid flow out of passageway 112 into transfer channel 110. The force of fluid flow travelling through passageway 112 causes the fluid flow to exit passageway 112 through opening 114. Fluid is expelled from passageway 112 and is utilized to facilitate transfer of tissue along transfer channel 110 in direction D1. Movement of fluid through opening 114 creates a hydraulic bearing surface at ends 74, 96 between cutter 64 and auger 66 to facilitate rotation of cutter 64 and prevent wear, overheating and/or damage during operation of the components of surgical instrument 12. In some embodiments, auger 66 is cannulated, but not fenestrated. In some embodiments, auger 66 has a solid configuration and is not cannulated or fenestrated.

Figure 10:
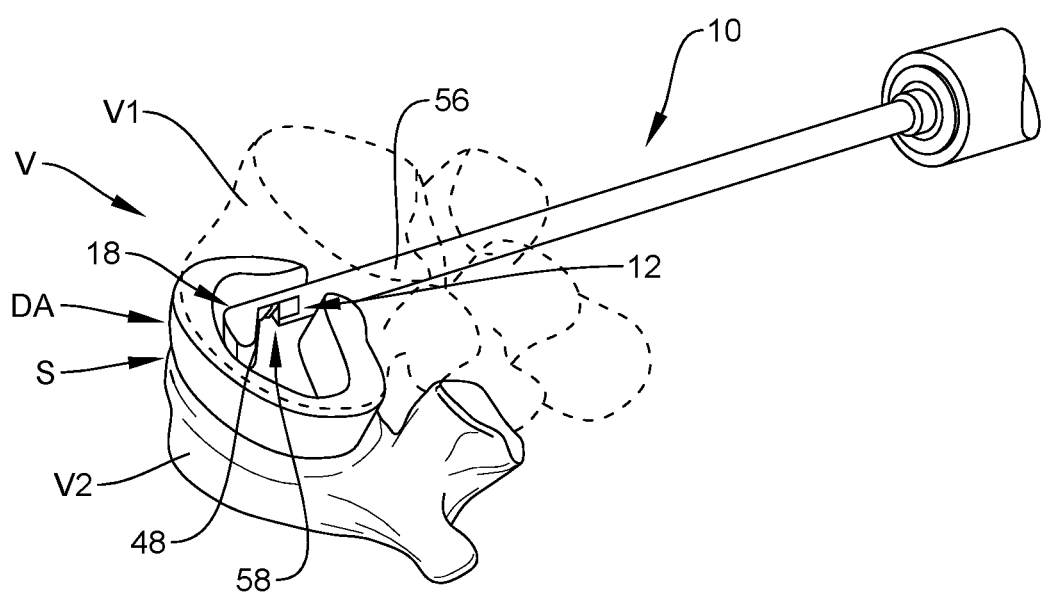
FIG. 10 is a perspective view, in part phantom, of components of one embodiment of a surgical system in accordance with the principles of the present disclosure disposed with vertebrae.

In assembly, operation and use, as shown in FIGS. 9 and 10, surgical system 10 is employed to treat an affected section of vertebrae V. A medical practitioner obtains access to a surgical site including vertebrae V in any appropriate manner, such as through incision and retraction of tissues. The components of surgical system 10 including surgical instrument 12 are employed to augment a surgical treatment. Surgical instrument 12 can be delivered to a surgical site as a pre-assembled device or can be assembled in situ. Surgical system 10 may be may be completely or partially revised, removed or replaced.

Surgical system 10 may be used with surgical methods or techniques including open surgery, mini-open surgery, minimally invasive surgery and percutaneous surgical implantation, whereby vertebrae V is accessed through a mini-incision, or sleeve that provides a protected passageway to the area. Once access to the surgical site is obtained, a surgical treatment, for example, corpectomy and/or discectomy, can be performed for treating a spine disorder. A diseased and/or damaged portion of vertebrae V between and/or including vertebra V1, V2, and diseased and/or damaged intervertebral discs and tissue are removed to create a vertebral space S.

Surgical instrument 12 is delivered to the surgical site including vertebrae V and inserted with space S. Handle 20 is manipulated to position end 18 of tube 14 with space S such that teeth 48 engage vertebral tissue, including but not limited to intervertebral tissue, endplate tissue and bone. For example, in one embodiment, handle 20 is manipulated to position end 18 of tube 14 within a disc annulus DA of vertebrae V within space S such that teeth 48 engage tissue of disc annulus DA, as shown in FIG. 10. Tube 14 is pulled in direction D1 using handle 20 such that teeth 48 to disrupt, scrape and/or remove tissue from the surgical site. The tissue moves into cavity 54, as discussed herein. In some embodiments, cavity 54 is angled toward opening 58 such that tissue that was scraped and/or removed by teeth 48 moves through opening 58 and into channel 40. Motor 26 is actuated to cause rotation of cutter 64 relative to auger 66.

Irrigation tube 36 is connected with port 32 and a source of fluid is connected to irrigation tube 36 to establish fluid flow in directions D1, D2, as described herein. Cutter 64 rotates relative to auger 66 such that blades 80 rotate to disrupt, scrape, cut, shear and/or macerate tissue that was scraped and/or removed by teeth 48 into a smaller particle size for removal the surgical site.

Blades 80 rotate such that tissue disposed adjacent and/or between cutter 64 and auger 66 is transferred and/or conveyed in direction D1 due to fluid transfer forces created between the helical configurations of cutter 64 and auger 66 and/or fluid exiting from opening 114. The dynamic fluid transfer and/or shear force created by rotation of cutter 64 relative to auger 66 and between helical blades 80 and helical surface 108 direct fluid and scraped tissue within transfer channel 110, to channel 40 as described herein.

Suction tube 34 is coupled to port 30 and a vacuum source such that the cut tissue and/or fluid is transferred and/or conveyed along channel 40 in the direction shown by arrow D1 for removal from the surgical site. The force of fluid and/or suction created by suction tube 34 directs the cut tissue and/or fluid through transfer channel 110 to channel 40. Fluid and/or tissue is/are pulled into suction tube 34 to remove the fluid and tissue from the surgical site.

In some embodiments, surgical system 10 can include one or more surgical instruments for use with surgical instrument 12, such as, for example, drivers, inserters, extenders, reducers, spreaders, distractors, blades, retractors, clamps, forceps, elevators and drills, which may be alternately sized and dimensioned, and arranged as a kit.

In one embodiment, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae V. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of surgical system 10 are removed and the incision is closed. The components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels.

Figure 11:
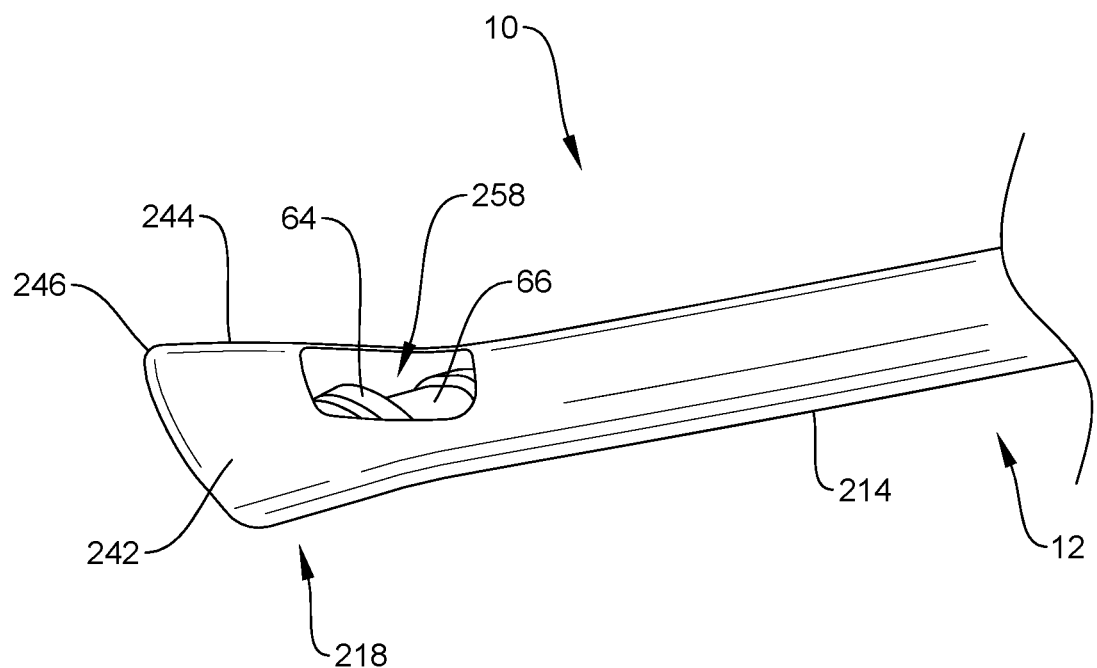
FIG. 11 is a perspective view of one embodiment of components of the system shown in FIG. 1 in accordance with the principles of the present disclosure.
Figure 12:
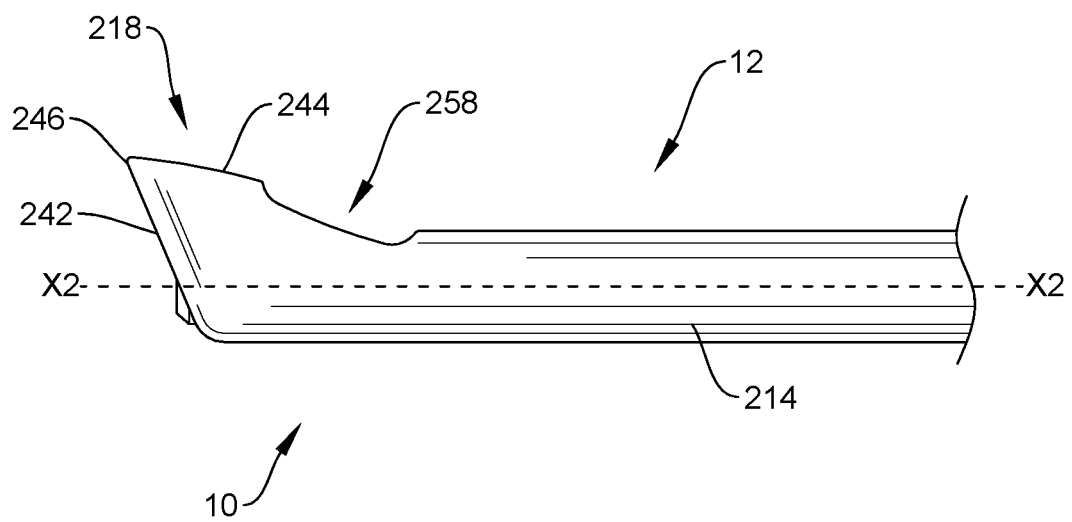
FIG. 12 is a side view of the components shown in FIG. 11.
Figure 13:
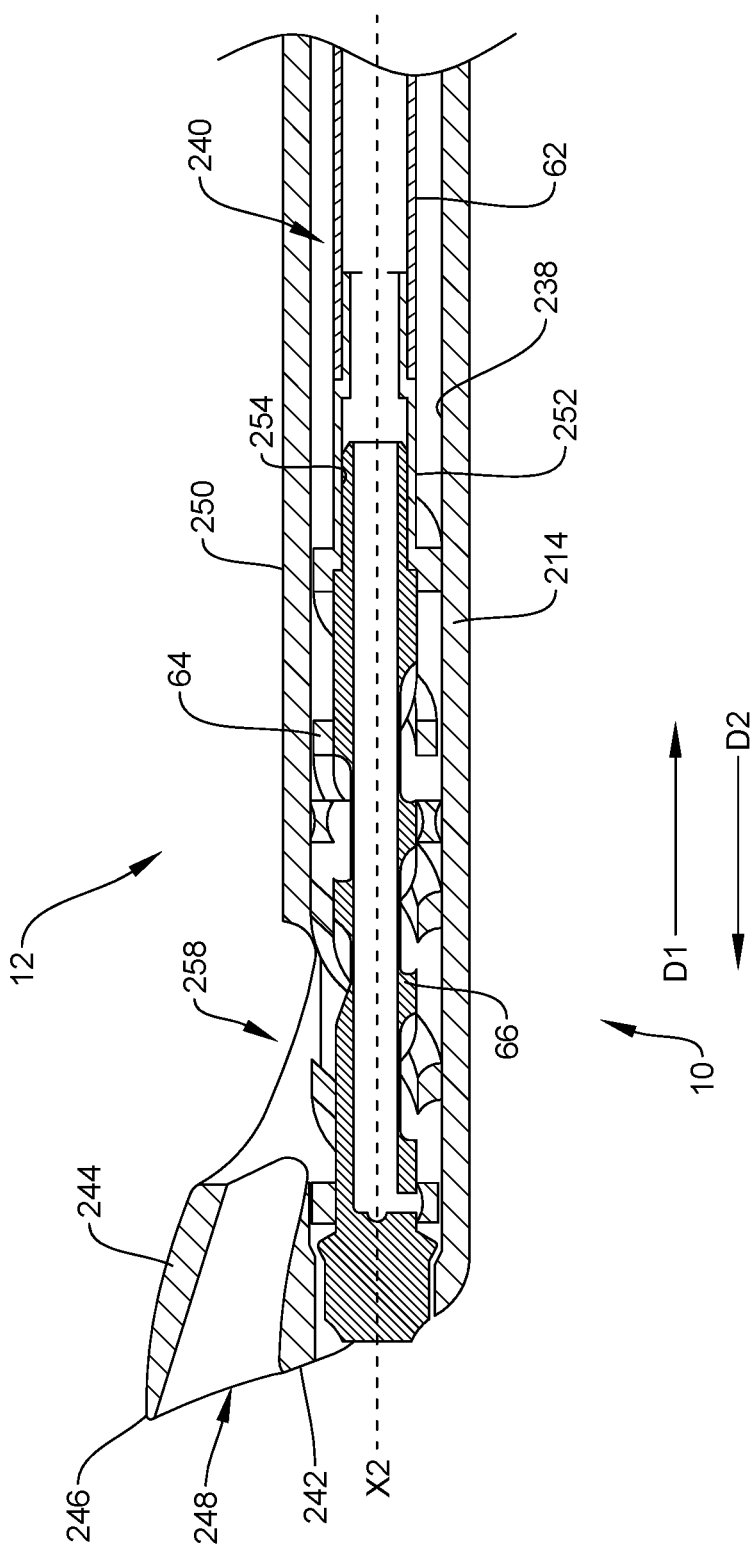
FIG. 13 is a side, cross-sectional view of the components shown in FIG. 11.

In one embodiment, as shown in FIGS. 11-13, system 10, similar to the systems and methods described herein, includes surgical instrument 12 having a scraper tube 214, similar to scraper tube 14 described herein. Tube 214 is coupled to handle 20 in the same or a similar manner that tube 14 is connected with handle 20. Tube 214 includes an inner surface 238 that defines a cavity, such as, for example, a channel 240. Channel 240 is configured for disposal of blade assembly 28. That is, tube 62, cutter 64 and auger 66 are each positioned in channel 240, as shown in FIG. 13. In some embodiments, channel 240 may have various cross section configurations, such as, for example, circular, cylindrical, oval, oblong, triangular, rectangular, square, polygonal, irregular, uniform, non-uniform, variable, tubular and/or tapered.

An end 218 of tube 214 extends transverse to a longitudinal axis X2 of tube 214 and includes a wall 242 and a wall 244. Wall 244 includes a cutting surface, such as, for example, a blade 246 configured to disrupt, scrape, cut and/or remove tissue from a surgical site. End 218 is angled such that blade 246 is positioned above a shaft 250 of tube 214. That is, end 218 has a maximum height that is greater than a maximum height of shaft 250 such that blade 246 is positioned above a shaft 250 of tube 214. Walls 242, 244 define an aperture 248 configured to move tissue that is disrupted, scraped, cut and/or removed by blade 246 into channel 240.

In one embodiment, auger 66 includes a threaded outer surface 252 that directly engages a threaded inner surface 254 of cutter 64 such that rotation of cutter 64 relative to auger 66 in a first rotational direction, such as, for example, clockwise causes cutter 64 to translate relative to auger 66 in direction D1 and rotation of cutter 64 relative to auger in an opposite second rotational direction, such as, for example, counterclockwise causes cutter 64 to translate relative to auger 66 in direction D2. In some embodiments, translation of cutter 64 relative to auger 66 in direction D1 facilitates movement of tissue and/or fluid from transfer channel 110 to channel 40 or 240. That is, translating cutter 64 relative to auger 66 in direction D1 will move tissue in transfer channel 110 in direction D1 such that the material moves from transfer channel 110 to channel 40 or 240.

Figure 14:
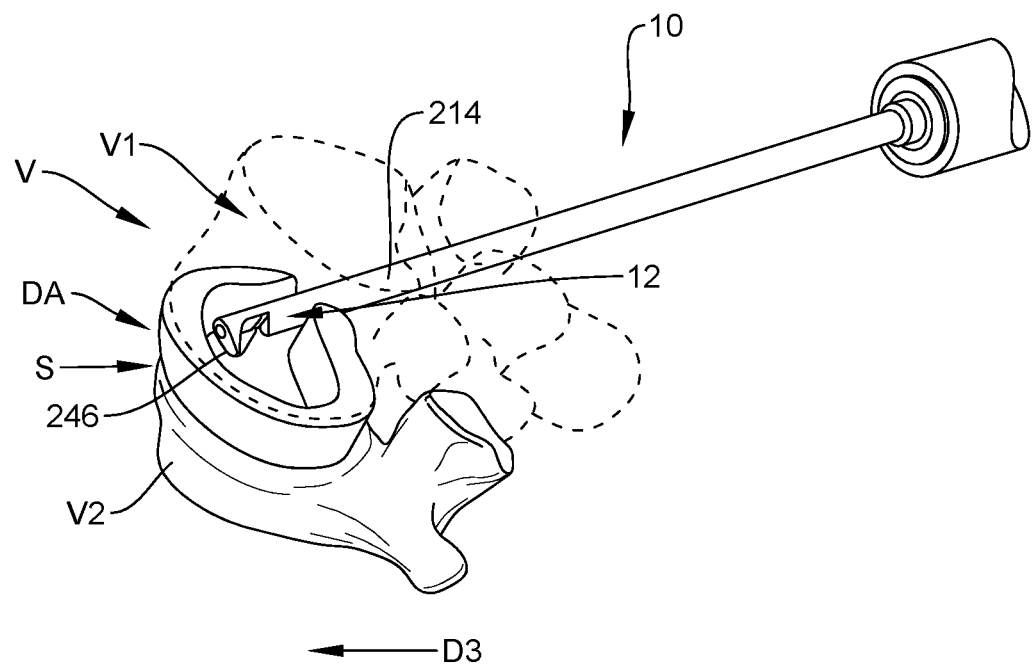
FIG. 14 is a perspective view, in part phantom, of components of one embodiment of a surgical system in accordance with the principles of the present disclosure disposed with vertebrae.

In operation and use, surgical instrument 12 is delivered to the surgical site including vertebrae V and inserted with space S. Handle 20 is manipulated to position end 218 of tube 214 with space S such that blade 246 engages vertebral tissue, including but not limited to intervertebral tissue, endplate tissue and bone. For example, in one embodiment, handle 20 is manipulated to position 218 of tube 214 within disc annulus DA of vertebrae V within space S, as shown in FIG. 14. Tube 214 is pushed in direction D3 using handle 20 such that blade 246 disrupts, scrapes and/or removes tissue from the surgical site. The tissue moves through aperture 248 and into transfer channel 110.

Irrigation tube 36 is connected with port 32 and a source of fluid is connected to the irrigation tube 36 to establish fluid flow in directions D1, D2, as described herein. Cutter 64 rotates relative to auger 66 such that blades 80 rotate to disrupt, scrape, cut, shear and/or macerate tissue that was scraped and/or removed by blade 246 into a smaller particle size for removal the surgical site.

Blades 80 rotate such that tissue disposed adjacent and/or between cutter 64 and auger 66 is transferred and/or conveyed in direction D1 due to fluid transfer forces created between the helical configurations of cutter 64 and auger 66 and/or fluid exiting from opening 114. The dynamic fluid transfer and/or shear force created by rotation and/or translation of cutter 64 relative to auger 66 and between helical blades 80 and helical surface 108 direct fluid and scraped tissue within transfer channel 110 into channel 240, as described herein.

Suction tube 34 is coupled to port 30 and a vacuum source. Tissue and/or fluid is transferred and/or conveyed along channel 240 in the direction shown by arrow D1 for removal from the surgical site. The force of fluid and/or suction created by suction tube 34 directs scraped tissue through transfer channel 110 to channel 240. Fluid mixed with tissue is pulled into suction tube 34 to remove the fluid and tissue from the surgical site.

In one embodiment, shown in FIGS. 15-19, surgical instrument 12 is similar to the embodiment of surgical instrument 12 shown in FIGS. 11-13, except that tube 214 has a blade assembly 328 positioned in channel 240 in place of blade assembly 28. Blade assembly 328 is configured for disposal in channel 240 such that blade assembly 328 is visible through an opening 258 of tube 214. Blade assembly 328 includes a shaft 362 that is configured to be coupled to motor 26 to rotate shaft 362 relative to tube 214 about axis X2. In some embodiments, shaft 362 is removably coupled to motor 26 such that shaft 362 can be removed from motor 26 without breaking shaft 362 and/or motor 26. In some embodiments, shaft 362 is permanently fixed with motor 26 such that shaft 362 cannot be removed from motor 26 without breaking shaft 362 and/or motor 26. For example, in some embodiments, shaft 362 is integrally and/or monolithically formed with an output shaft of motor 26. Shaft 362 extends along axis X2 when disposed in channel 240. Blade assembly 328 includes a member, such as, for example, a rotatable cutter 364 that is coupled to shaft 362 and a member, such as, for example, a stationary auger 366. In some embodiments, auger 366 is integrally and/or monolithically formed with tube 214 such that auger 366 is permanently affixed to tube 214.

Figure 15:
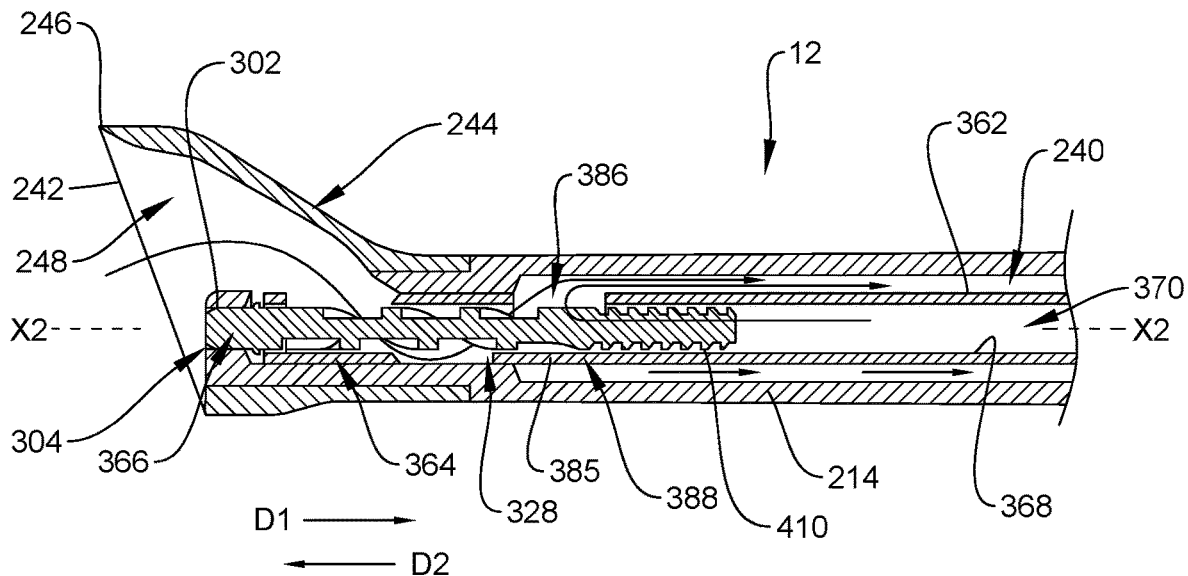
FIG. 15 is a side, cross-sectional view of one embodiment of components of the system shown in FIG. 1 in accordance with the principles of the present disclosure.
Figure 16:
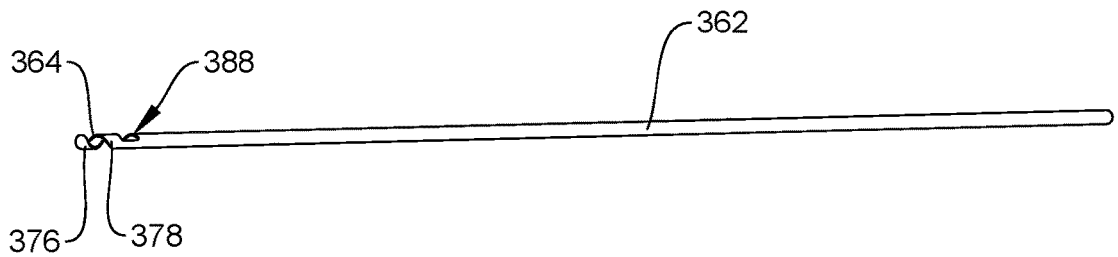
FIG. 16 is a perspective view of a component of the system shown in FIG. 15.
Figure 17:
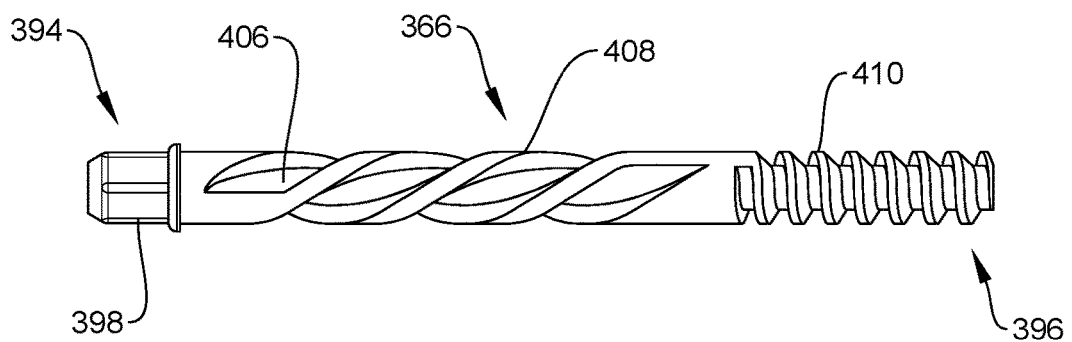
FIG. 17 is a perspective view of a component of the system shown in FIG. 15.
Figure 18:
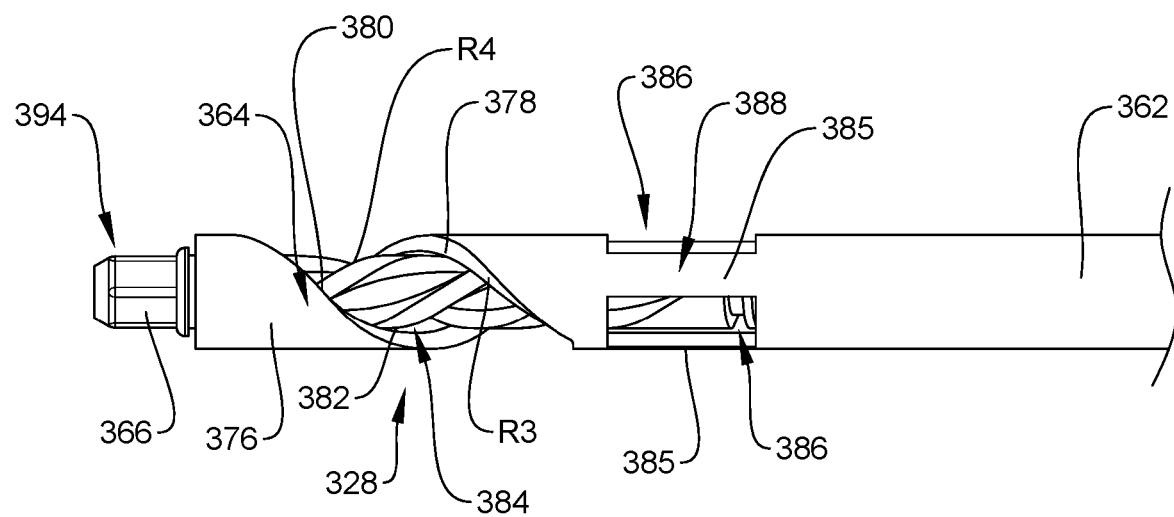
FIG. 18 is a side view of components of the system shown in FIG. 15.
Figure 19:
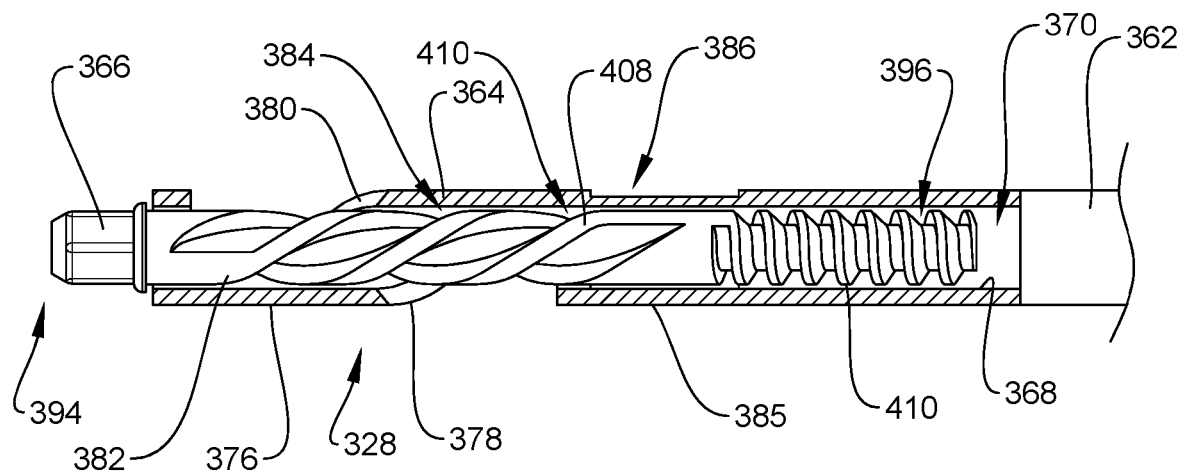
FIG. 19 is a side view, in part phantom, of components of the system shown in FIG. 15.

Cutter 364 is fixed relative to shaft 362 such that rotation of shaft 362 relative to tube 214 about axis X2 also rotates cutter 364 relative to tube 214 about axis X2. In some embodiments, shaft 362 is removably coupled to cutter 364 such that shaft 362 can be removed from cutter 364 without breaking shaft 362 and/or cutter 364. In some embodiments, shaft 362 is permanently fixed with cutter 364 such that shaft 362 cannot be removed from cutter 364 without breaking shaft 362 and/or cutter 364. For example, in some embodiments, shaft 362 is integrally and/or monolithically formed with cutter 364. Shaft 362 includes an inner surface 368 defining a passageway 370, as best shown in FIG. 15. In some embodiments, cutter 364 can be variously connected with shaft 362, such as, for example, monolithic, integral connection, frictional engagement, threaded engagement, mutual grooves, screws, adhesive, nails, barbs and/or raised element. Cutter 364 extends along axis X2 when disposed in channel 240. Cutter 364 is tubular in configuration. In some embodiments, cutter 364 may have cross section configurations, such as, for example, oval, cylindrical, triangular, square, polygonal, irregular, uniform, non-uniform, offset, staggered, undulating, arcuate, variable and/or tapered.

Cutter 364 includes a surface 376 defining a cutting flute 378 that forms a single helical blade 380 extending along a length of cutter 364. Helical blade 380 is disposed at a rotational pitch R3. In some embodiments, surface 376 includes a scaffold and/or network of blades. In some embodiments, blade 380 may be disposed at alternate relative orientations, such as, for example, parallel, transverse and/or other angular orientations such as acute or obtuse, co-axial and/or may be offset or staggered. Blade 380 is configured for rotation within channel 240 and about auger 366 to disrupt, scrape, cut, shear and/or macerate tissue and/or transfer and/or convey tissue along auger 366, as described herein. In some embodiments, cutter 364 includes a section, such as, for example, a solid ring section 65, shown in FIG. 8, for example. In some embodiments, cutter 364 is configured to force tissue under cutter 364 and through flutes of auger 366 defined by a helical surface 408 of auger 366. This controls the tissue entering a discharge side of cutter 364 into a suction and/or vacuum pathway, as discussed herein.

Cutter 364 includes an inner surface 382 that defines an interior cavity 384. Cavity 384 is in communication with passageway 370. In some embodiments, cavity 384 is coaxial with passageway 370. Cavity 384 is configured for disposal of auger 366 within channel 240, as described herein. Cutter 364 is configured for rotation relative to tube 214 and auger 366 to transfer tissue along a first direction, such as, for example, a direction D1 (FIG. 15) along axis X2, as described herein. In some embodiments, blade 380 rotates relative to tube 214 and auger 366 within channel 240 to move tissue in aperture 248 that was disrupted, scraped, cut, sheared and/or macerated by blade 246 into a smaller particle size for removal from a surgical site. In some embodiments, blade 380 rotates such that tissue disposed adjacent and/or between cutter 364 and auger 366 is transferred and/or conveyed in direction D1 due to fluid transfer forces created between the helical configurations of cutter 364 and auger 366. The tissue is transferred and/or conveyed for removal from a surgical site, as described herein. In some embodiments, auger 366 comprises two or more counter rotating internal blades. In some embodiments, the blades are co-axially disposed and comprise alternate diameters, increasing or decreasing. In some embodiments, the blades are separate and disposed in a serial configuration. In some embodiments, the blades may rotate in the same or different directions.

In some embodiments, shaft 362 includes a plurality of spaced apart openings 386 that each extend through a thickness of wall 244. Openings 386 are defined by spaced apart ribs 385. Openings 386 are disposed circumferentially about shaft 362 to define a grinder 388 configured to grind scraped tissue that was cut by cutter 364 and/or auger 66. Grinder 388 can include one or a plurality of openings 386. Grinder 388 is integrally and/or monolithically formed with shaft 362 and cutter 364. As such, upon rotation of shaft 362 relative to tube 214 and auger 366, blade 380 cuts tissue and causes tissue within cavity 384 to move in the direction shown by arrow D1 such that the tissue within cavity 384 moves into grinder 388, where it is ground into smaller pieces. In some embodiments, edges of ribs 385 that define openings 386 are sharpened to form blades to facilitate the grinding of tissue when shaft 362 is rotated relative to tube 214 and auger 366. In some embodiments, openings 386 are uniformly spaced apart from one another. For example, in one embodiment, shaft 362 includes three openings 386 that are each spaced apart 120 degrees from an adjacent opening 386. In some embodiments, openings 386 are variously shaped, such as, for example, oval, oblong, triangular, rectangular, square, polygonal, irregular, uniform, non-uniform, offset, staggered, undulating, arcuate, variable and/or tapered.

Auger 366 extends between an end 394 and an end 396 along axis X2 when disposed in channel 240. Auger 366 is configured for disposal with cavity 384. Auger 366 is fixed with end 218 of tube 214. That is, auger 366 is coupled to tube 214 such that auger 366 is prevented from rotating and/or translating relative to tube 214. In some embodiments, end 394 includes an engagement portion 398 configured for engagement with tube 214 to fix auger 366 relative to tube 214. In some embodiments, portion 398 may include a square, triangular, polygonal, star, torx, or hexalobe cross sectional configuration configured engage a correspondingly shaped portion of tube 214, such as, for example, a surface 302 of tube 214. For example, in some embodiments, surface 302 defines an aperture 304 having a cross section that corresponds to the cross sectional configuration of portion 398 to resist and/or prevent rotation of auger 366 relative to tube 214. In some embodiments, portion 398 is positioned within aperture 304 such that an outer surface of portion 398 directly engages surface 302 to resist and/or prevent rotation of auger 366 relative to tube 214.

Auger 366 includes a surface 406 that defines helical surface 408. Helical surface 408 is disposed in an alternate orientation relative to helical blade 380. Helical surface 408 includes a rotational pitch R4 that is alternative to rotational pitch R3 to create a dynamic fluid transfer and/or shear force or pressure to transfer and/or convey tissue from a surgical in direction D1. Helical blade 380 and helical surface 408 form a transfer channel 410 therebetween configured to direct cut tissue along axis X2 in direction D1. The dynamic fluid transfer and/or shear force created by rotation of cutter 364 relative to auger 366 and between helical blade 380 and helical surface 408 direct fluid flow and scraped or cut tissue within transfer channel 410. In some embodiments, surface 376 and/or surface 406 may comprise alternate configurations, such as, for example, grooved, channeled, undulating, even, uniform, non-uniform, offset, staggered, textured and/or tapered to facilitate directional flow of fluid. In one embodiment, auger 366 includes fiber-optic light cable (not shown) disposed and/or helically wound through a surface of auger 366. The light-cable illuminates a surgical site. In some embodiments, an illumination device may be mounted with various components of surgical instrument 12. In one embodiment, a miniature camera (not shown) can be mounted with various components of surgical instrument 12 to facilitate imaging of the surgical site.

In some embodiments, auger 366 has a solid configuration and is free of any cannulas or passageways that are coaxial with a body of auger 366. That is, auger 366 is not cannulated or fenestrated. End 396 includes a helical irrigation flute 410 configured to move irrigation fluid within passageway 370 to move in the direction shown by arrow D2 (FIG. 15) such that the irrigation fluid exits passageway 370. Suction within channel 240 then causes the irrigation fluid and/or any scraped or cut tissue within passageway 370 to move in the direction shown by arrow D1 for disposal thereof.

In operation and use, surgical instrument 12 is delivered to the surgical site including vertebrae V and inserted with space S. Handle 20 is manipulated to position end 218 of tube 214 with space S such that blade 246 engages vertebral tissue, including but not limited to intervertebral tissue, endplate tissue and bone. For example, in one embodiment, handle 20 is manipulated to position 218 of tube 214 within disc annulus DA of vertebrae V within space S, as shown in FIG. 14. Tube 214 is pushed in direction D3 using handle 20 such that blade 246 disrupts, scrapes and/or removes tissue from the surgical site. The tissue moves through aperture 248 and into transfer channel 110.

Irrigation tube 36 is connected with port 32 and a source of fluid is connected to the irrigation tube 36 to establish fluid flow in directions D1, D2, as described herein. Cutter 364 rotates relative to auger 366 such that blade 380 rotates to disrupt, scrape, cut, shear and/or macerate tissue that was scraped and/or removed by blade 246 into a smaller particle size for removal the surgical site.

Blade 380 rotates such that tissue disposed adjacent and/or between cutter 364 and auger 366 is transferred and/or conveyed in direction D1 due to fluid transfer forces created between the helical configurations of cutter 364 and auger 366. The dynamic fluid transfer and/or shear force created by rotation and/or translation of cutter 364 relative to auger 366 and between helical blade 380 and helical surface 408 direct fluid and scraped tissue into channel 240, as described herein.

Suction tube 34 is coupled to port 30 and a vacuum source. Tissue and/or fluid is transferred and/or conveyed along channel 240 in the direction shown by arrow D1 for removal from the surgical site. The force of fluid and/or suction created by suction tube 34 directs scraped tissue to channel 240. Fluid mixed with tissue is pulled into suction tube 34 to remove the fluid and tissue from the surgical site.

Figure 20:
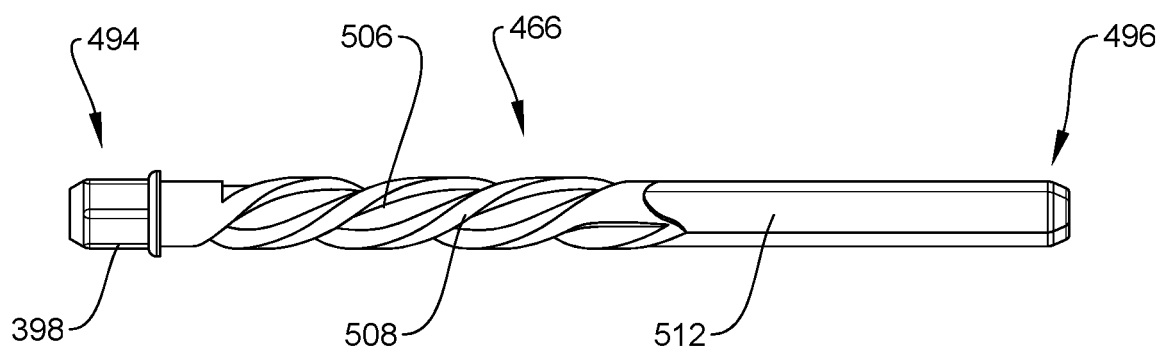
FIG. 20 is a perspective view of one embodiment of a component of the system shown in FIG. 15 in accordance with the principles of the present disclosure.
Figure 21:
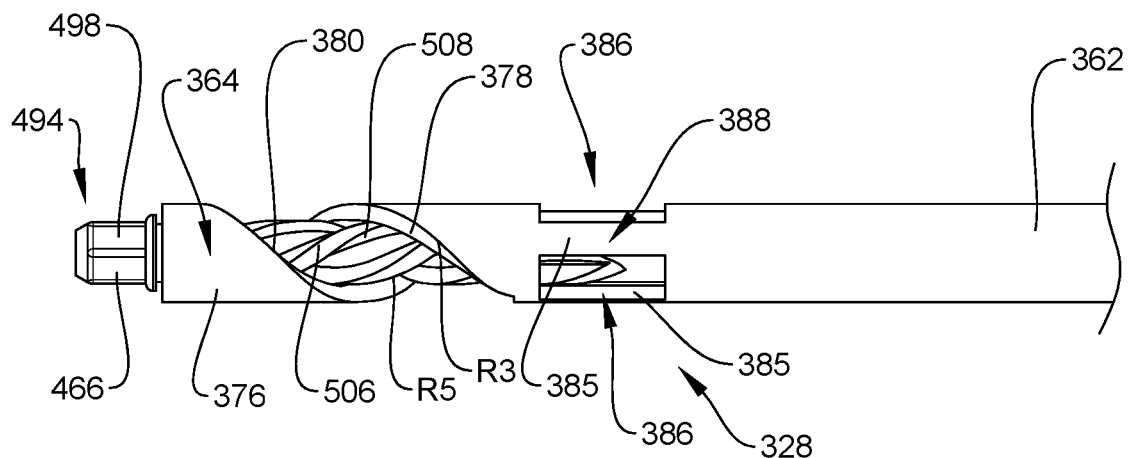
FIG. 21 is a side view of the components shown in FIGS. 16 and 20.
Figure 22:
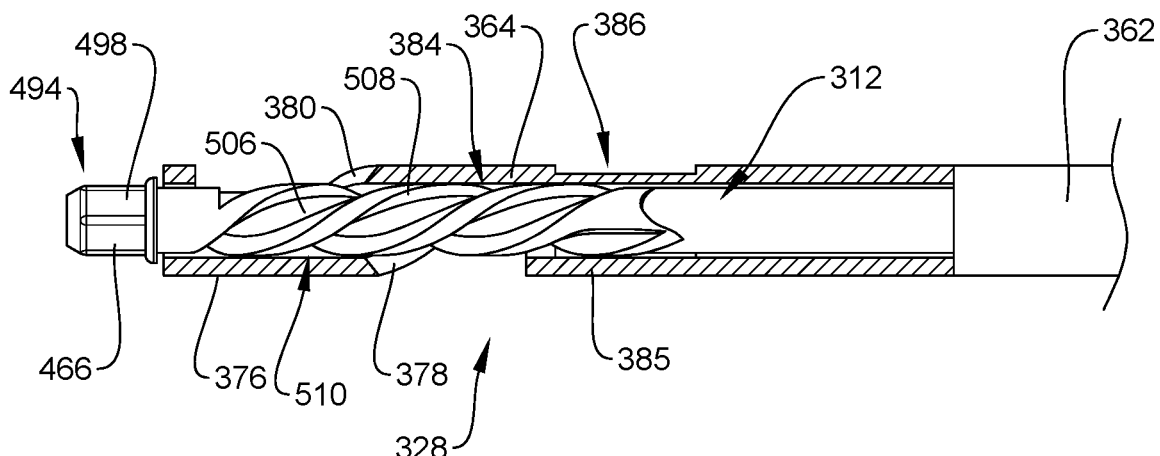
FIG. 22 is a side view, in part phantom, of the components shown in FIGS. 16 and 20.

In one embodiment, shown in FIGS. 20-22, surgical instrument 12 is similar to the embodiment of surgical instrument 12 shown in FIGS. 15-19, except that blade assembly 328 includes an auger 466 in place of auger 366. Auger 466 extends between an end 494 and an end 496 along axis X2 when disposed in channel 240. Auger 466 is configured for disposal with cavity 384. Auger 466 is fixed with end 218 of tube 214. That is, auger 466 is coupled to tube 214 such that auger 366 is prevented from rotating and/or translating relative to tube 214. In some embodiments, end 494 includes an engagement portion 498 configured for engagement with tube 214 to fix auger 466 relative to tube 214. In some embodiments, portion 498 may include a square, triangular, polygonal, star, torx, or hexalobe cross sectional configuration configured engage a correspondingly shaped portion of tube 214, such as, for example, surface 302 of tube 214. For example, in some embodiments, aperture 304 has a cross section that corresponds to the cross sectional configuration of portion 498 to resist and/or prevent rotation of auger 466 relative to tube 214. In some embodiments, portion 498 is positioned within aperture 304 such that an outer surface of portion 498 directly engages surface 302 to resist and/or prevent rotation of auger 466 relative to tube 214.

Auger 466 includes a surface 506 that defines helical surface 508. Helical surface 508 is disposed in an alternate orientation relative to helical blade 380. Helical surface 508 includes a rotational pitch R5 that is alternative to rotational pitch R3 to create a dynamic fluid transfer and/or shear force or pressure to transfer and/or convey tissue from a surgical in direction D1. Helical blade 380 and helical surface 508 form a transfer channel 510 therebetween configured to direct cut tissue along axis X2 in direction D1. The dynamic fluid transfer and/or shear force created by rotation of cutter 364 relative to auger 466 and between helical blade 380 and helical surface 508 direct fluid flow and scraped or cut tissue within transfer channel 510. In some embodiments, surface 376 and/or surface 506 may comprise alternate configurations, such as, for example, grooved, channeled, undulating, even, uniform, non-uniform, offset, staggered, textured and/or tapered to facilitate directional flow of fluid. In one embodiment, auger 466 includes fiber-optic light cable (not shown) disposed and/or helically wound through a surface of auger 466. The light-cable illuminates a surgical site. In some embodiments, an illumination device may be mounted with various components of surgical instrument 12. In one embodiment, a miniature camera (not shown) can be mounted with various components of surgical instrument 12 to facilitate imaging of the surgical site.

In some embodiments, auger 466 has a solid configuration and is free of any cannulas or passageways that are coaxial with a body of auger 466. That is, auger 466 is not cannulated or fenestrated. End 496 includes one or a plurality of straight irrigation flutes 512 configured to move irrigation fluid within passageway 370 to move in the direction shown by arrow D2 (FIG. 15) such that the irrigation fluid exits passageway 370. Suction within channel 240 then causes the irrigation fluid and/or any scraped or cut tissue within passageway 370 to move in the direction shown by arrow D1 for disposal thereof. In some embodiments, flutes 512 are disposed evenly around the diameter of end 496. For example, in one embodiment, auger 466 includes three flutes 512 disposed circumferentially about end 496 such that flues 512 are each spaced apart 120 degrees from an adjacent one of flutes 510. In some embodiments, flutes 512 are concave grooves. In some embodiments, flutes 512 may be variously configured and dimensioned, such as, for example, planar, concave, polygonal, irregular, uniform, non-uniform, staggered, tapered, consistent or variable, depending on the requirements of a particular application.

Figure 23:
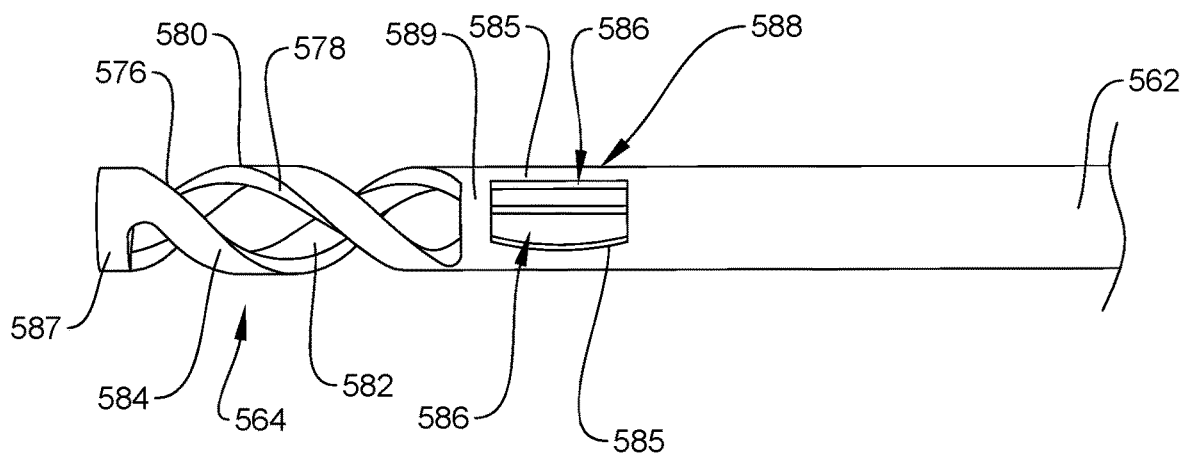
FIG. 23 is a side view of one embodiment of a component of the system shown in FIG. 15 in accordance with the principles of the present disclosure.

In one embodiment, shown in FIG. 23, surgical instrument 12 is similar to the embodiment of surgical instrument 12 shown in FIGS. 11-19, except that blade assembly 328 includes a shaft 562 in place of shaft 362, a cutter 564 in place of cutter 364, and a grinder 588 in place of grinder 388. Cutter 564 is coupled to shaft 562. Shaft 562 is configured to be coupled to motor 26 to rotate shaft 562 relative to tube 214 about axis X2. In some embodiments, shaft 562 is removably coupled to motor 26 such that shaft 562 can be removed from motor 26 without breaking shaft 562 and/or motor 26. In some embodiments, shaft 562 is permanently fixed with motor 26 such that shaft 562 cannot be removed from motor 26 without breaking shaft 562 and/or motor 26. For example, in some embodiments, shaft 562 is integrally and/or monolithically formed with an output shaft of motor 26. Shaft 562 extends along axis X2 when disposed in channel 240. Cutter 564 is fixed relative to shaft 562 such that rotation of shaft 562 relative to tube 214 about axis X2 also rotates cutter 564 relative to tube 214 about axis X2. In some embodiments, shaft 562 is removably coupled to cutter 564 such that shaft 562 can be removed from cutter 564 without breaking shaft 562 and/or cutter 564. In some embodiments, shaft 562 is permanently fixed with cutter 564 such that shaft 562 cannot be removed from cutter 564 without breaking shaft 562 and/or cutter 564. For example, in some embodiments, shaft 562 is integrally and/or monolithically formed with cutter 564. Shaft 562 includes an inner surface defining a passageway. In some embodiments, cutter 564 can be variously connected with shaft 562, such as, for example, monolithic, integral connection, frictional engagement, threaded engagement, mutual grooves, screws, adhesive, nails, barbs and/or raised element. Cutter 564 extends along axis X2 when disposed in channel 240. Cutter 564 is tubular in configuration. In some embodiments, cutter 564 may have cross section configurations, such as, for example, oval, cylindrical, triangular, square, polygonal, irregular, uniform, non-uniform, offset, staggered, undulating, arcuate, variable and/or tapered.

Cutter 564 includes a cutting flute 576 and a cutting flute 578 that forms a double helical blade 580 extending along a length of cutter 564. In some embodiments, flute 576 is joined with flute 578 at a circular ring 587 at a first end of cutter 564 and flute 576 is joined with flute 578 at a circular ring 589 at a second end of cutter 564. In some embodiments, blade 580 may be disposed at alternate relative orientations, such as, for example, parallel, transverse and/or other angular orientations such as acute or obtuse, co-axial and/or may be offset or staggered. Blade 580 is configured for rotation within channel 240 and about auger 366 to disrupt, scrape, cut, shear and/or macerate tissue and/or transfer and/or convey tissue along auger 366, as described herein. In some embodiments, cutter 564 is configured to force tissue under cutter 564 and through flutes of auger 366 defined by helical surface 408 of auger 366. This controls the tissue entering a discharge side of cutter 564 into a suction and/or vacuum pathway, as discussed herein.

Cutter 564 includes an inner surface 582 that defines an interior cavity 584. Cavity 584 is in communication with the passageway of shaft 562. In some embodiments, cavity 584 is coaxial with the passageway of shaft 562. Cavity 584 is configured for disposal of auger 366 within channel 240, as described herein. Cutter 564 is configured for rotation relative to tube 214 and auger 366 to transfer tissue along a first direction, such as, for example, a direction D1 along axis X2, as described herein. In some embodiments, blade 580 rotates relative to tube 214 and auger 366 within channel 240 to move tissue in aperture 248 that was disrupted, scraped, cut, sheared and/or macerated by blade 580 into a smaller particle size for removal from a surgical site. In some embodiments, blade 580 rotates such that tissue disposed adjacent and/or between cutter 564 and auger 366 is transferred and/or conveyed in direction D1 due to fluid transfer forces created between the helical configurations of cutter 564 and auger 366. The tissue is transferred and/or conveyed for removal from a surgical site, as described herein.

In some embodiments, shaft 562 includes a plurality of spaced apart openings 586 that each extend through a thickness of shaft 562. Openings 586 are defined by spaced apart ribs 585. Openings 586 are disposed circumferentially about shaft 562 to define grinder 588. Grinder 588 is configured to grind scraped tissue that was cut by cutter 564 and/or auger 366. Grinder 588 can include one or a plurality of openings 586. Grinder 588 is integrally and/or monolithically formed with shaft 562 and cutter 564. As such, upon rotation of shaft 562 relative to tube 214 and auger 366, blade 580 cuts tissue and causes tissue within cavity 584 to move in the direction shown by arrow D1 such that the tissue within cavity 584 moves into grinder 588, where it is ground into smaller pieces. In some embodiments, edges of ribs 585 that define openings 586 are sharpened to form blades to facilitate the grinding of tissue when shaft 562 is rotated relative to tube 214 and auger 366. In some embodiments, ribs 585 each extend parallel to one another such that ribs 585 each extend parallel to axis X2 when cutter 564 is positioned within channel 240. In some embodiments, openings 586 are uniformly spaced apart from one another. For example, in one embodiment, shaft 562 includes three openings 586 that are each spaced apart 120 degrees from an adjacent opening 586. In some embodiments, openings 586 are variously shaped, such as, for example, oval, oblong, triangular, rectangular, square, polygonal, irregular, uniform, non-uniform, offset, staggered, undulating, arcuate, variable and/or tapered.

Figure 24:
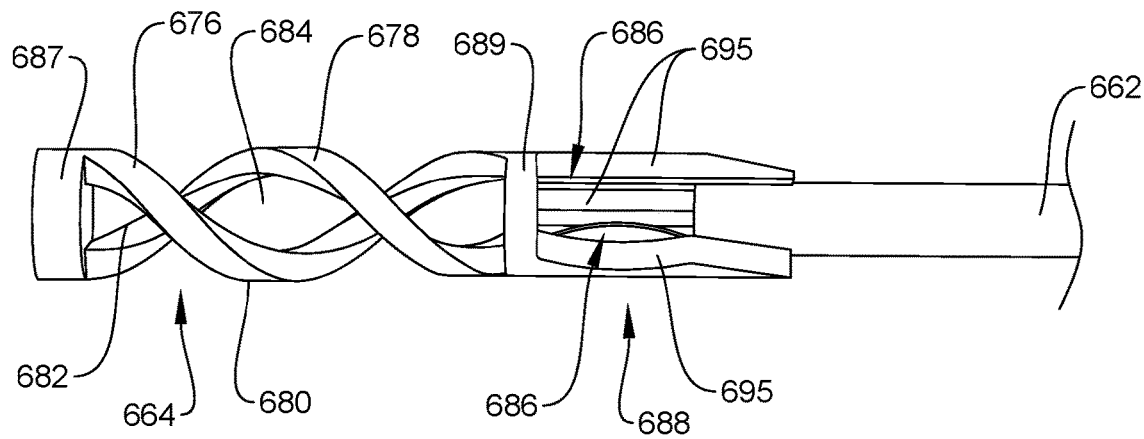
FIG. 24 is a side view of one embodiment of a component of the system shown in FIG. 15 in accordance with the principles of the present disclosure.

In one embodiment, shown in FIG. 24, surgical instrument 12 is similar to the embodiment of surgical instrument 12 shown in FIGS. 11-19, except that blade assembly 328 includes a shaft 662 in place of shaft 362, a cutter 664 in place of cutter 364, and a grinder 688 in place of grinder 388. Cutter 664 is coupled to shaft 662. Shaft 662 is configured to be coupled to motor 26 to rotate shaft 662 relative to tube 214 about axis X2. In some embodiments, shaft 662 is removably coupled to motor 26 such that shaft 662 can be removed from motor 26 without breaking shaft 662 and/or motor 26. In some embodiments, shaft 662 is permanently fixed with motor 26 such that shaft 662 cannot be removed from motor 26 without breaking shaft 662 and/or motor 26. For example, in some embodiments, shaft 662 is integrally and/or monolithically formed with an output shaft of motor 26. Shaft 662 extends along axis X2 when disposed in channel 240. Cutter 664 is fixed relative to shaft 662 such that rotation of shaft 662 relative to tube 214 about axis X2 also rotates cutter 664 relative to tube 214 about axis X2. In some embodiments, shaft 662 is removably coupled to cutter 664 such that shaft 662 can be removed from cutter 664 without breaking shaft 662 and/or cutter 664. In some embodiments, shaft 662 is permanently fixed with cutter 664 such that shaft 662 cannot be removed from cutter 664 without breaking shaft 662 and/or cutter 664. For example, in some embodiments, shaft 662 is integrally and/or monolithically formed with cutter 664. Shaft 662 includes an inner surface 668 defining a passageway. In some embodiments, cutter 564 can be variously connected with shaft 562, such as, for example, monolithic, integral connection, frictional engagement, threaded engagement, mutual grooves, screws, adhesive, nails, barbs and/or raised element. Cutter 564 extends along axis X2 when disposed in channel 240. Cutter 564 is tubular in configuration. In some embodiments, cutter 564 may have cross section configurations, such as, for example, oval, cylindrical, triangular, square, polygonal, irregular, uniform, non-uniform, offset, staggered, undulating, arcuate, variable and/or tapered.

Cutter 664 includes a cutting flute 576 and a cutting flute 678 that forms a double helical blade 680 extending along a length of cutter 664. In some embodiments, cutting flute 576 is joined with cutting flute 678 at a circular ring 687 at a first end of cutter 664 and cutting flute 576 is joined with cutting flute 678 at a circular ring 689 at a second end of cutter 664. In some embodiments, blade 680 may be disposed at alternate relative orientations, such as, for example, parallel, transverse and/or other angular orientations such as acute or obtuse, co-axial and/or may be offset or staggered. Blade 680 is configured for rotation within channel 240 and about auger 366 to disrupt, scrape, cut, shear and/or macerate tissue and/or transfer and/or convey tissue along auger 366, as described herein. In some embodiments, cutter 664 is configured to force tissue under cutter 664 and through flutes of auger 366 defined by helical surface 408 of auger 366. This controls the tissue entering a discharge side of cutter 664 into a suction and/or vacuum pathway, as discussed herein.

Cutter 664 includes an inner surface 582 that defines an interior cavity 684. Cavity 684 is in communication with the passageway of shaft 662. In some embodiments, cavity 684 is coaxial with the passageway of shaft 662. Cavity 684 is configured for disposal of auger 366 within channel 240, as described herein. Cutter 664 is configured for rotation relative to tube 214 and auger 366 to transfer tissue along a first direction, such as, for example, a direction D1 along axis X2, as described herein. In some embodiments, blade 680 rotates relative to tube 214 and auger 366 within channel 240 to move tissue in aperture 248 that was disrupted, scraped, cut, sheared and/or macerated by blade 680 into a smaller particle size for removal from a surgical site. In some embodiments, blade 680 rotates such that tissue disposed adjacent and/or between cutter 664 and auger 366 is transferred and/or conveyed in direction D1 due to fluid transfer forces created between the helical configurations of cutter 664 and auger 366. The tissue is transferred and/or conveyed for removal from a surgical site, as described herein.

In some embodiments, shaft 662 is connected to ring 689 by a plurality of spaced apart fingers 695. Fingers 695 define openings 686 therebetween. Openings 686 define grinder 688. Grinder 688 is configured to grind scraped tissue that was cut by cutter 664 and/or auger 366. Grinder 688 can include one or a plurality of openings 686. Grinder 688 is integrally and/or monolithically formed with shaft 662 and cutter 664. As such, upon rotation of shaft 662 relative to tube 214 and auger 366, blade 680 cuts tissue and causes tissue within cavity 684 to move in the direction shown by arrow D1 such that the tissue within cavity 684 moves into grinder 688, where it is ground into smaller pieces. In some embodiments, fingers 695 each extend parallel to one another such that fingers 695 each extend parallel to axis X2 when cutter 664 is positioned within channel 240. In some embodiments, edges of fingers 695 that define openings 686 are sharpened to form blades to facilitate the grinding of tissue when shaft 662 is rotated relative to tube 214 and auger 366. In some embodiments, openings 686 are uniformly spaced apart from one another. For example, in one embodiment, grinder 688 includes three openings 686 that are each spaced apart 120 degrees from an adjacent opening 686. In some embodiments, openings 686 are variously shaped, such as, for example, oval, oblong, triangular, rectangular, square, polygonal, irregular, uniform, non-uniform, offset, staggered, undulating, arcuate, variable and/or tapered.

Figure 25:
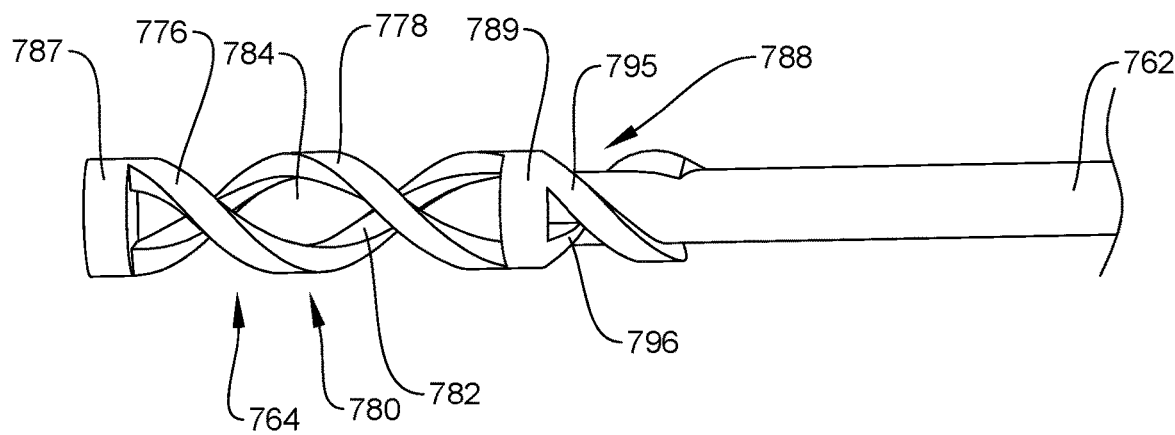
FIG. 25 is a side view of one embodiment of a component of the system shown in FIG. 15 in accordance with the principles of the present disclosure.

In one embodiment, shown in FIG. 25, surgical instrument 12 is similar to the embodiment of surgical instrument 12 shown in FIGS. 11-19, except that blade assembly 328 includes a shaft 762 in place of shaft 362, a cutter 764 in place of cutter 364, and a grinder 788 in place of grinder 388. Cutter 764 is coupled to shaft 762. Shaft 762 is configured to be coupled to motor 26 to rotate shaft 762 relative to tube 214 about axis X2. In some embodiments, shaft 762 is removably coupled to motor 26 such that shaft 762 can be removed from motor 26 without breaking shaft 762 and/or motor 26. In some embodiments, shaft 762 is permanently fixed with motor 26 such that shaft 762 cannot be removed from motor 26 without breaking shaft 762 and/or motor 26. For example, in some embodiments, shaft 762 is integrally and/or monolithically formed with an output shaft of motor 26. Shaft 762 extends along axis X2 when disposed in channel 240. Cutter 764 is fixed relative to shaft 762 such that rotation of shaft 762 relative to tube 214 about axis X2 also rotates cutter 764 relative to tube 214 about axis X2. In some embodiments, shaft 762 is removably coupled to cutter 764 such that shaft 762 can be removed from cutter 764 without breaking shaft 762 and/or cutter 764. In some embodiments, shaft 762 is permanently fixed with cutter 764 such that shaft 762 cannot be removed from cutter 764 without breaking shaft 762 and/or cutter 764. For example, in some embodiments, shaft 762 is integrally and/or monolithically formed with cutter 764. Shaft 762 includes an inner surface defining a passageway. In some embodiments, cutter 764 can be variously connected with shaft 762, such as, for example, monolithic, integral connection, frictional engagement, threaded engagement, mutual grooves, screws, adhesive, nails, barbs and/or raised element. Cutter 764 extends along axis X2 when disposed in channel 240. Cutter 764 is tubular in configuration. In some embodiments, cutter 764 may have cross section configurations, such as, for example, oval, cylindrical, triangular, square, polygonal, irregular, uniform, non-uniform, offset, staggered, undulating, arcuate, variable and/or tapered.

Cutter 764 includes a cutting flute 776 and a cutting flute 778 that forms a double helical blade 780 extending along a length of cutter 764. In some embodiments, flute 776 is joined with flute 778 at a circular ring 787 at a first end of cutter 764 and flute 776 is joined with flute 778 at a circular ring 789 at a second end of cutter 764. In some embodiments, blade 780 may be disposed at alternate relative orientations, such as, for example, parallel, transverse and/or other angular orientations such as acute or obtuse, co-axial and/or may be offset or staggered. Blade 780 is configured for rotation within channel 240 and about auger 366 to disrupt, scrape, cut, shear and/or macerate tissue and/or transfer and/or convey tissue along auger 366, as described herein. In some embodiments, cutter 764 is configured to force tissue under cutter 764 and through flutes of auger 366 defined by helical surface 408 of auger 366. This controls the tissue entering a discharge side of cutter 764 into a suction and/or vacuum pathway, as discussed herein.

Cutter 764 includes an inner surface 782 that defines an interior cavity 784. Cavity 784 is in communication with the passageway of shaft 762. In some embodiments, cavity 784 is coaxial with the passageway of shaft 762. Cavity 784 is configured for disposal of auger 366 within channel 240, as described herein. Cutter 764 is configured for rotation relative to tube 214 and auger 366 to transfer tissue along a first direction, such as, for example, a direction D1 along axis X2, as described herein. In some embodiments, blade 780 rotates relative to tube 214 and auger 366 within channel 240 to move tissue in aperture 248 that was disrupted, scraped, cut, sheared and/or macerated by blade 780 into a smaller particle size for removal from a surgical site. In some embodiments, blade 780 rotates such that tissue disposed adjacent and/or between cutter 764 and auger 366 is transferred and/or conveyed in direction D1 due to fluid transfer forces created between the helical configurations of cutter 764 and auger 366. The tissue is transferred and/or conveyed for removal from a surgical site, as described herein.

In some embodiments, shaft 762 is connected to ring 789 by a flute 795 and a flute 796. Flutes 795, 796 define one or a plurality of openings 786. Openings 786 define grinder 788. Grinder 788 is configured to grind scraped tissue that was cut by cutter 764 and/or auger 366. Grinder 788 can include one or a plurality of openings 786. Grinder 788 is integrally and/or monolithically formed with shaft 762 and cutter 764. As such, upon rotation of shaft 762 relative to tube 214 and auger 366, blade 780 cuts tissue and causes tissue within cavity 784 to move in the direction shown by arrow D1 such that the tissue within cavity 784 moves into grinder 788, where it is ground into smaller pieces. In some embodiments, edges of flutes 795, 796 that define openings 786 are sharpened to form blades to facilitate the grinding of tissue when shaft 762 is rotated relative to tube 214 and auger 366.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method comprising:
    providing a surgical instrument, the surgical instrument comprising a shaft, a first blade positioned within the shaft and a second blade positioned within the first blade, the shaft extending along a longitudinal axis from a proximal end to an opposite distal end, the distal end comprising a scraping surface defining a plurality of teeth;
    engaging the teeth with bone;
    moving the shaft relative to the bone to scrape tissue from the bone; and
    rotating the first blade relative to the second blade to grind the scraped tissue into ground tissue.

2. The method recited in claim 1, wherein the scraped tissue has a first particle size and the ground tissue has a second particle size, the second particle size being less than the first particle size.

3. The method recited in claim 1, further comprising moving fluid though the shaft to move the scraped tissue within the shaft prior to rotating the first blade relative to the second blade.

4. The method recited in claim 1, wherein the shaft comprises a port and the method further comprises coupling an irrigation tube to the port and connecting a source of fluid to the irrigation tube to establish fluid flow that moves the scraped tissue proximally along the longitudinal axis within the shaft prior to rotating the first blade relative to the second blade.

5. The method recited in claim 1, further comprising creating suction within the shaft to move the ground tissue within the shaft proximally along the longitudinal axis.

6. The method recited in claim 1, wherein the shaft comprises a port and the method further comprises coupling a suction tube to the port and connecting a vacuum source to the suction tube to move the ground tissue proximally along the longitudinal axis within the shaft.

7. The method recited in claim 1, wherein rotating the first blade relative to the second blade comprises rotating the first blade relative to the shaft and the second blade.

8. The method recited in claim 1, wherein the bone is a vertebra and moving the shaft relative to the bone to scrape tissue from the bone comprises moving the shaft relative to the vertebra to scrape tissue within a disc annulus of the vertebra.

9. The method recited in claim 1, wherein moving the shaft relative to the bone to scrape tissue from the bone comprises pulling the shaft.

10. The method recited in claim 1, wherein the second blade is fixed to the shaft.

11. The method recited in claim 1, wherein the blades each include a plurality of spaced cutting flutes.

12. The method recited in claim 1, wherein the blades each have a helical configuration.

13. The method recited in claim 1, wherein the scraping surface extends transverse to the longitudinal axis.

14. The method recited in claim 1, wherein the surgical instrument comprises a motor that is actuated to rotate the first blade relative to the second blade to grind the scraped tissue into ground tissue.

15. The method recited in claim 1, wherein the first blade is positioned entirely within the shaft.

16. The method recited in claim 1, wherein the scraping surface extends transverse to the longitudinal axis, the first blade being positioned entirely within the shaft, and the second blade being fixed relative to the shaft.

17. The method recited in claim 1, wherein an end of the second blade extends through an aperture of the shaft.

18. The method recited in claim 1, wherein the second blade includes a threaded surface that directly engages a threaded surface of the first blade such that the first blade translates relative to the second blade along the longitudinal axis as the first blade rotates relative to the second blade.

19. A method comprising:
providing a surgical instrument, the surgical instrument comprising a shaft, a first helical blade positioned entirely within the shaft and a second helical blade positioned within the first blade, the first blade being rotatable relative to the shaft, the second blade being fixed relative to the shaft, the shaft extending along a longitudinal axis from a proximal end to an opposite distal end, the distal end comprising a scraping surface defining a plurality of teeth, the scraping surface extending transverse to the longitudinal axis;
engaging the teeth with bone;
moving the shaft relative to the bone to scrape tissue from the bone;
moving fluid though the shaft to move the scraped tissue within the shaft;
rotating the first blade relative to the second blade to grind the scraped tissue into ground tissue; and
creating suction within the shaft to move the ground tissue within the shaft proximally along the longitudinal axis.

20. A method comprising:
providing a surgical instrument, the surgical instrument comprising a shaft, a first helical blade positioned entirely within the shaft and a second helical blade positioned within the first blade, the first blade being rotatable relative to the shaft, the second blade being fixed relative to the shaft, the shaft extending along a longitudinal axis from a proximal end to an opposite distal end, the distal end comprising a scraping surface defining a plurality of teeth, the scraping surface extending transverse to the longitudinal axis;
engaging the teeth with bone;
moving the shaft relative to the bone to scrape tissue from the bone;
coupling an irrigation tube to a port of the shaft and connecting a source of fluid to the irrigation tube to establish fluid flow that moves the scraped tissue proximally along the longitudinal axis within the shaft prior;
rotating the first blade relative to the second blade to grind the scraped tissue into ground tissue; and
coupling a suction tube to the port and connecting a vacuum source to the suction tube to move the ground tissue proximally along the longitudinal axis within the shaft.

* * * * *